(12) United States Patent
Nelson et al.

(10) Patent No.: US 12,329,774 B2
(45) Date of Patent: Jun. 17, 2025

(54) METHOD AND COMPOSITION FOR ENHANCING THE QUALITY AND BENEFITS OF SLEEP

(71) Applicant: BioLink Life Sciences, Inc., Cary, NC (US)

(72) Inventors: Deanna J. Nelson, Raleigh, NC (US); James R. Komorowski, Trumbull, CT (US)

(73) Assignee: BioLink Life Sciences, Inc., Cary, NC (US)

( * ) Notice: Subject to any disclaimer, the term of this patent is extended or adjusted under 35 U.S.C. 154(b) by 513 days.

(21) Appl. No.: 17/222,953

(22) Filed: Apr. 5, 2021

(65) Prior Publication Data
US 2021/0308081 A1 Oct. 7, 2021

Related U.S. Application Data

(60) Provisional application No. 63/005,080, filed on Apr. 3, 2020.

(51) Int. Cl.
| | |
|---|---|
| A61K 33/06 | (2006.01) |
| A23L 33/10 | (2016.01) |
| A23L 33/16 | (2016.01) |
| A61K 9/00 | (2006.01) |
| A61K 31/191 | (2006.01) |
| A61P 25/20 | (2006.01) |

(52) U.S. Cl.
CPC ............. *A61K 33/06* (2013.01); *A23L 33/10* (2016.08); *A23L 33/16* (2016.08); *A61K 9/0019* (2013.01); *A61K 9/0053* (2013.01); *A61K 31/191* (2013.01); *A61P 25/20* (2018.01)

(58) Field of Classification Search
CPC .... A61K 33/06; A61K 9/0019; A61K 9/0053; A61K 31/191; A23L 33/10; A23L 33/16; A61P 25/20
See application file for complete search history.

(56) References Cited

U.S. PATENT DOCUMENTS

| | | | |
|---|---|---|---|
| 4,013,699 A * | 3/1977 | Passedouet | C07F 5/069 |
| | | | 556/179 |
| 5,501,866 A | 3/1996 | Kakuda et al. | |
| 10,335,384 B2 | 7/2019 | Henderson et al. | |
| 10,449,148 B2 | 10/2019 | Gutierrez et al. | |
| 10,517,322 B1 | 12/2019 | Lee | |
| 2001/0001307 A1 * | 5/2001 | Ueda | A61K 31/198 |
| | | | 514/563 |
| 2002/0122835 A1 | 9/2002 | Bucci et al. | |
| 2006/0246129 A1 | 11/2006 | Linardakis et al. | |
| 2008/0009505 A1 * | 1/2008 | Hodges | A61P 25/28 |
| | | | 426/597 |
| 2008/0039526 A1 * | 2/2008 | Ozeki | A23G 3/48 |
| | | | 514/563 |
| 2015/0320814 A1 | 11/2015 | Patel et al. | |
| 2020/0121624 A1 * | 4/2020 | Liu | A61K 33/06 |

FOREIGN PATENT DOCUMENTS

| | | |
|---|---|---|
| CN | 102827896 | 12/2012 |
| JP | 2005-289948 | 10/2005 |
| WO | WO-2003/090738 | 11/2003 |
| WO | WO-2006/090640 | 8/2006 |

OTHER PUBLICATIONS

Grodowska et al. "Organic Solvents in the Pharmaceutical Industry". 2010. Acta Poloniae Pharmaceutical. 67(1): 3-12. (Year: 2010).*
Gupta et al. Salts of Therapeutic Agents: Chemical, Physicochemical, and Biological Considerations. Molecules. 23(1719): 1-15. (Year: 2018).*
Kakuda et al. "Inhibiting Effects of Theanine on Caffeine Stimulation Evaluated by EEG in the Rat". IBiosci. Biotechnol. Biochem., 64(2):287-293 (Year: 2000).*
STN Compound Entry Date (Year: 2021).*
Abbasi et al., "The effect of magnesium supplementation on primary insomnia in elderly: A double-blind placebo-controlled clinical trial," J Res Med Sci., 2012; 17(12): pp. 1161-1169. PubMed PMID: 23853635; PubMed Central PMCID: PMC3703169.
Ates et al., "Dose-dependent absorption profile of different magnesium compounds," Biol Trace Elem Res., 2019; 192(2): pp. 244-251.
Coskuner et al., "Adenosine triphosphate (ATP) reduces amyloid-β protein misfolding in vitro," J Alzheimers Dis., 2014; 41(2): pp. 561-574. PubMed PMID: 24625803.
Deckert et al., "Adenosinergic psychopharmaceuticals?" Trends Pharmacol Sci., 1989; 10: pp. 99-100.
Ding et al., "Changes in the composition of brain interstitial ions control the sleep-wake cycle," Science, 2016; 352(6285): pp. 550-555.
Dominguez et al., "Nutritional prevention of cognitive decline and dementia," Acta Biomed., 2018; 89(2): pp. 276-290.
Hafner et al., "Why sleep matters—the economic costs of insufficient sleep. A cross-country comparative analysis," Rand Corp., Santa Monica, CA; 2016.
Haskell et al., "The effects of L-theanine, caffeine and their combination on cognition and mood," Biol Psychol., 2008; 77(2): pp. 113-122. PubMed PMID: 18006208.
International Search Report and Written Opinion issued in PCT/US2021/025836, mailed Jun. 30, 2021.
Jackson et al, "The requirement for bivalent cations in formation of nicotinamide-adenine dinucleotide by nicotinamide mononucleotide adenylyltransferase of pig-liver nuclei," Biochem J., 1966;101(1): pp. 208-213.
Jang et al., "L-theanine partially counteracts caffeine-induced sleep disturbances in rats," Pharmacol Biochem Behav., 2012; 101(2): pp. 217-221.
Jo et al., "Polygonatum sibiricum rhizome promotes sleep by regulating nonrapid eye movement and GABAergic/serotonergic receptors in rodent models," Biomed Pharmacother., Sep. 2018; 105: pp. 167-175.

(Continued)

*Primary Examiner* — Jeffrey S Lundgren
*Assistant Examiner* — Ibrahim D Bori
(74) *Attorney, Agent, or Firm* — Casimir Jones, S.C.; J. Mitchell Jones

(57) ABSTRACT

Compounds, compositions and methods of making and using for enhancing the quality and benefit of sleep and/or wakefulness in a subject in need thereof.

5 Claims, 11 Drawing Sheets

(56) References Cited

OTHER PUBLICATIONS

Kakuda, "Neuroprotective effects of theanine and its preventive effects on cognitive dysfunction," Pharmacol Res., Aug. 2011; 64(2): pp. 162-168. PubMed PMID: 21477654.

Kim et al., "GABA and l-theanine mixture decreases sleep latency and improves NREM sleep," Pharm Biol. 2019; 57(1): 64-72.

Kimura et al., "L-Theanine reduces psychological and physiological stress responses," Biol Psychol., Jan. 2007; 74(1): pp. pp. 39-45. PubMed PMID: 16930802.

Lawless et al., "The taste of calcium and magnesium salts and anionic modifications," Food Qual Prefer, 2003; 14: pp. 319-325.

Nathan et al. "The neuropharmacology of L-theanine (N-ethyl-L-glutamine): a possible neuroprotective and cognitive enhancing agent," J Herb Pharmacother., 2006; 6(2): pp. 21-30. PubMed PMID: 17182482.

NIH State-of-the-Science Conference Statement on manifestations and management of chronic insomnia in adults. NIH Consens State Sci Statements., Jun. 13-15, 2005; 22(2): pp. 1-30.

Paterson et al., "A translational, caffeine induced model of onset insomnia in rats and healthy volunteers," Psychopharmacology (Berlin) 2007; 191: pp. 943-950.

Sharma et al., "L-Theanine: An astounding sui generis integrant in tea," Food Chem., 2018; 242: pp. 601-610. PubMed PMID: 29037735.

Shinomiya et al., "Effects of chlorogenic acid and its metabolites on the sleep-wakefulness cycle in rats," Eur J Pharmacol, 2004; 504: pp. 185-189.

Wiedmann et al., "Pharmaceutical salts: Theory, use in solid dosage forms and in situ preparation in an aerosol," Asian J Pharm. Sci., 2016; 11: pp. 722-734.

Xiong et al., "Erythrocyte intracellular Mg(2+) concentration as an index of recognition and memory," Sci Rep., 2016; 6: pp. 1-12. doi: 10.1038/srep26975.

\* cited by examiner

| | Sleep Cycle (a 90 minute cycle that repeats 4-6 times over 6-7 hours of sleep) | | | | | |
|---|---|---|---|---|---|---|
| Sleepiness | NREM | | | | REM | Wakefulness |
| | N1 | N2 | N3 | N2 | | |
| | | Typically, the longest period of SWS | Longer early in sleep | | Dreaming | |
| Enhanced by melatonin secretion from the pineal gland and adenosine release from the basal forebrain | Periods of slow wave sleep (SWS) characterized by:<br>• Decreased body temperature<br>• Decreased heart rate<br>• Decreased brain oxygen consumption<br>• Muscle relaxation<br><br>Functions during SWS:<br>1. Restoration<br>• Healing<br>• Synthesis of anabolic proteins (e.g., growth hormone, prolactin)<br>• Glycogen synthesis<br>• ATP synthesis<br>• Removal of metabolic wastes<br>2. Memory processing (formation of long-term memory) Theta activity Hippocampus to cortex processing<br>3. Dreaming (REM activity) | | | | Reduced muscle activity (peripheral muscle "paralysis"), longer REM periods at the end of the 6-7 hour sleep cycle | Mediated by concerted release of neuromodulators (norepinephrine, acetylcholine, histamine, dopamine, and orexin) from neurons located in the brainstem, hypothalamus, and basal forebrain |

FIG. 1

| Sleep Cycle (a 90 minute cycle that repeats 4-6 times over 6-7 hours of sleep) | | | | | | |
|---|---|---|---|---|---|---|
| Sleepiness | NREM | | | REM | Wakefulness | |
| | N1 | N2 | N3 | N2 | | |
| | "Wake mouse" model | | | | | |
| L-Theanine (20mg/kg) significantly decreased sleep latency | L-Theanine (20 mg/kg) significantly increased sleep time. At same dose, significantly increased REM time. With single dose, no change in NREM time. However, with chronic administration, significant increase in NREM time. Actions included an increase in theta waves and a decrease in delta waves during N1, followed by increases in delta waves during subsequent stages | | | | | |
| | Arousal animal model | | | | | |
| | Theanine significantly increased GABAA receptors and increased GABAB receptors. Concurrently theanine increased both the GluR1 and GluN1 receptor subunits | | | | | |

FIG. 2

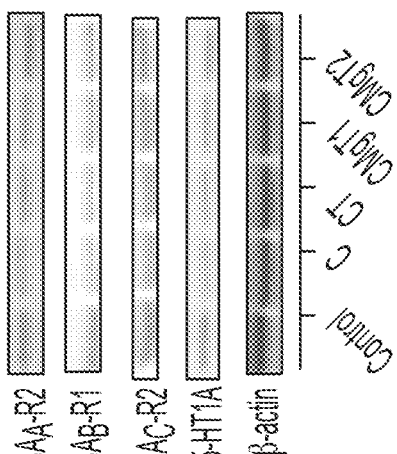
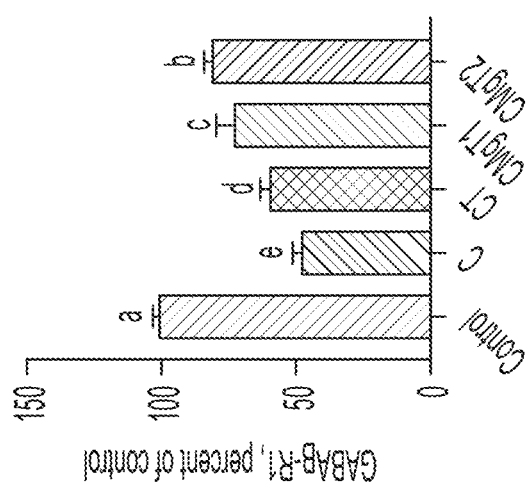
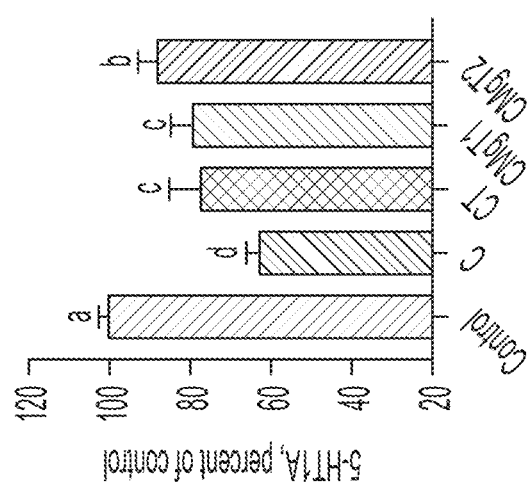
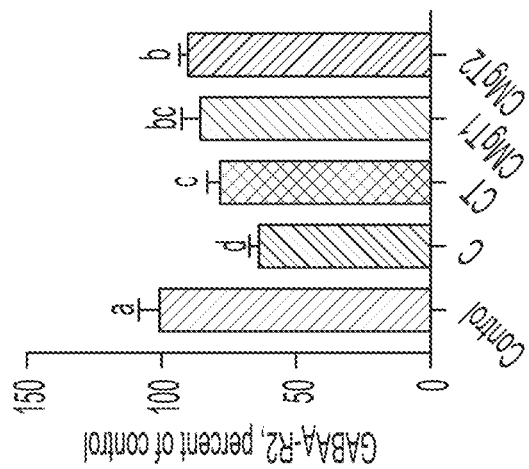
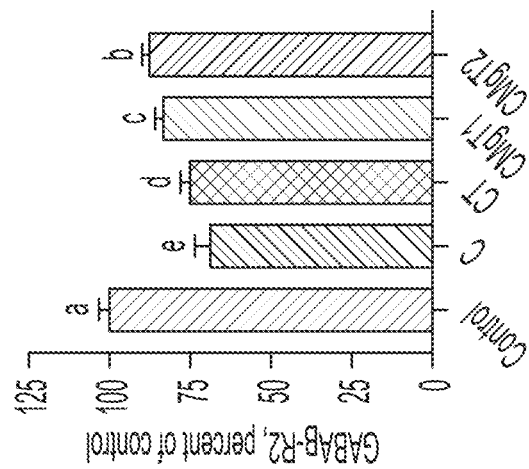

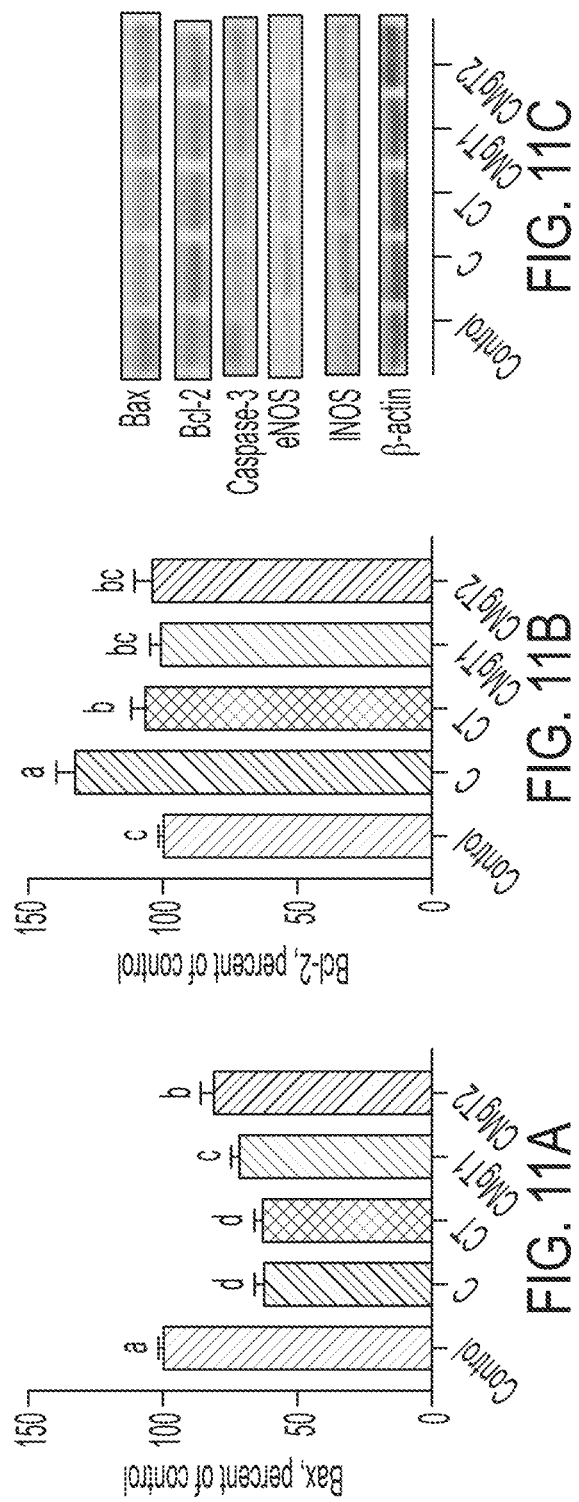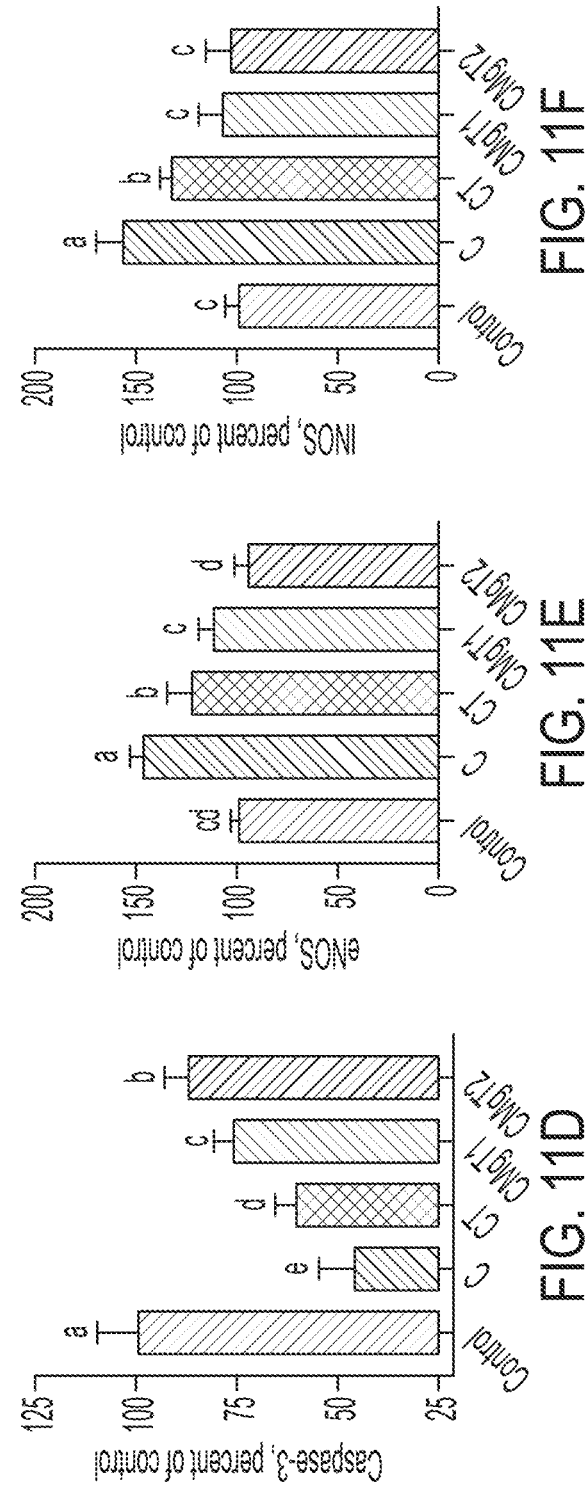

METHOD AND COMPOSITION FOR ENHANCING THE QUALITY AND BENEFITS OF SLEEP

CROSS-REFERENCE TO RELATED APPLICATIONS

This Application claims the benefit of U.S. Provisional Application 63/005,080 filed on Apr. 3, 2020. The entire contents of this application is incorporated herein by reference in its entirety.

FIELD OF THE INVENTION

The present application relates to magnesium di-L-theanate compositions and methods of use. The methods and compositions disclosed herein are particularly useful for providing bioavailable magnesium and L-theanine to mammals and treating or preventing sleep disorders.

BACKGROUND

Sleep is a naturally recurring state of mind and body, characterized by reduced perception of external stimuli, reduced muscle activity, and slowed rate of breathing and heart rate. Sleep typically occurs in 4-6 repeating periods over 6-7 hours, in which the body alternates between two physiologically distinct modes: non-Rapid Eye Movement (NREM) sleep and REM sleep. The former mode, also described as periods of slow wave sleep (SWS), is characterized by decreased body temperature, decreased heart rate, muscle relaxation and decreased brain oxygen consumption. During SWS the brain undergoes restoration and healing, including synthesis of anabolic proteins (e.g., growth hormone, prolactin); glycogen synthesis; adenosine triphosphate (ATP) synthesis; removal of metabolic wastes; and memory processing. The REM mode of sleep includes dreaming.

Sleep is a complex and dynamic process that affects how a subject functions during wakefulness. For example, one of the central functions of sleep is consolidation of long-term memory. This process involves not only strengthening of certain neural connections but also reducing memories that the brain deems unimportant. During consolidation both positive and negative memories may be reinforced, establishing an association between sleep patterns and depression during wakefulness. Likewise, during sleep the volume and movement of the lymphatic system of the brain increases. This increase provides opportunities for removal of metabolic waste, including misfolded proteins and other toxins. Sleep also beneficially affects higher cortical function and cognition; conversely, sleep deprivation reduces attention to decision-making, ability to multi-task, and performance of tasks that rely on memory. Somewhat surprisingly, sleep also enhances creativity, and sleep deprivation reduces it. Finally, sleep affects physical health and longevity from childhood through adult life. Sleep supports brain growth and maturation in childhood. In adults, sleep plays vital roles in regulating mood, appetite, muscle tissue health and function, and libido. Moreover, in adults, sleep deprivation has been associated with seven of the fifteen leading causes of death in the United States, including cardiovascular disease, malignant neoplasm, cerebrovascular disease, accidents, diabetes, septicemia and hypertension.

A wide variety of drugs are available to treat dysfunctional sleep. However, the U.S. National Institutes of Health has declared that drugs used routinely for treatment of sleep disorders have more hazards than benefits and have, therefore, not recommended them for elderly individuals, one of the largest groups experiencing sleep disorders.[18]

The Centers for Disease Control and Prevention (CDC) in the United States has declared insufficient sleep a "public health problem." Indeed, according to a recent CDC study, more than a third of American adults are not getting enough sleep on a regular basis.[7] The RAND research group estimates that between lost work and poor performance at work from lack of sleep, the U.S. alone loses at least $411 billion each year.[7] These repercussions stem from people being unwell because of it, which underlines the very real consequences of poor quality of sleep. As the research shows, sleep isn't a luxury it's a necessity for maintaining health and well-being throughout life.

In 2018 Sharma et al. stated an unmet need for a natural nutraceutical formulation having sleep induction properties, indicating that the need for methods and compositions to enhance the quality and benefits of sleep remains current.[20] The present invention provides a method and composition that satisfies the unmet need for enhancement of the quality and benefits of sleep.

SUMMARY OF THE INVENTION

Certain embodiments of the invention related to a magnesium di-L-theanate composition and methods of using the composition. In certain embodiments, effective amounts of a composition are administered in methods to enhance qualities of sleep and/or wakefulness in a mammal. Other embodiments include methods of administering effective amounts of a composition provided herein to enhance the benefits of sleep and/or wakefulness.

One embodiment of the invention includes a method of administering an effective amount of a composition to decrease a mammal's sleep latency period, the period before the onset of sleep. This decrease reflects a composition-related reduction in excitatory effects that delay the onset of sleep. In another embodiment, an effective amount of a magnesium di-L-theanate composition of the invention is administered to a mammal in need thereof to increase the length of sleep. If the duration of sleep has been decreased by some known or unknown factor, the composition restores the duration of sleep to the normal period expected by the mammal.

In yet another embodiment of the invention, an effective amount of a magnesium di-L-theanate composition of the invention is administered to enhance slow wave sleep in a mammal. In certain embodiments of the invention, benefits seen following the methods of administration of the composition are increases in the amplitude of brain waves monitored and decreases in the spike frequency of electrical activity disrupting sleep during this period.

In some embodiments, administration of effective amounts of a magnesium di-L-theanate composition of the invention restores the concentration of key neurotransmitters in the brain. This action enhances the quality and benefits of sleep of a mammal.

In another embodiment of the invention, an effective amount of a magnesium di-L-theanate composition of the invention effects reduction in the adverse effects of stress, oxidative stress, and metabolic disruption in the brain of a mammal. Reduction enhances the quality and benefits of sleep. Also, reduction supports brain cell survival after stress, including remediation of apoptotic damage to the brain of the mammal. Reduction protects brain tissue and functionality during periods of stress, oxidative stress, and metabolic disruption in the brain.

Another embodiment of the invention is that an effective amount of a magnesium di-L-theanate composition of the invention restores and maintains functionality of neurotransmitters in the brain. These actions protect and support normal brain function, during both sleep and wakefulness.

BRIEF DESCRIPTION OF THE DRAWINGS

The accompanying drawings, which are included to provide a further understanding of the invention and are incorporated in and constituted a part of this specification, illustrate preferred embodiments of the invention and together with the detail description serve to explain the principles of the invention. In the drawings:

FIG. 1 is a graphic depiction of a typical adult sleep cycle.

FIG. 2 is a summary of published information regarding the effects of L-theanine on components of an adult sleep cycle, both in the caffeine-induced "wake rodent" model and in the pentobarbital-induced sleep model.

FIG. 9(A-E). Effect of different forms of theanine on GABAA-R2 (9A), GABAB-R1 (9B), GABAB-R2 (9D) and 5-HT1A (9E) protein levels in caffeine-induced wakefulness mice. GABAA-R2: GABA type A receptor 2, GABAB-R1: GABA type B receptor 1, GABAB-R2: GABA type B receptor 2; 5-HT1A: 5-hydroxytryptamine type A receptor 1. Data are expressed as percent of the control value. Blots were repeated at least 3 times. Western blot (9C) analysis was performed with actin included to ensure equal protein loading. Data are presented as a bar graph with means and standard deviations. a-e: Values within the bars with different subscripts are significantly different (ANOVA and Turkey's post-hoc test).

FIG. 11(A-F). Effect of different forms of theanine on Bax (11A), Bcl-2 (11B), Caspase-3 (11D), eNOS (11E) and iNOS (11F) protein levels in caffeine-induced wakefulness mice. Data are expressed as percent of the control value. Blots were repeated at least 3 times. Western blot (11C) analysis was performed with actin included to ensure equal protein loading. Data are presented as a bar graph with means and standard deviations. a-e: Values within the bars with different subscripts are significantly different (ANOVA and Turkey's post-hoc test).

DETAILED DESCRIPTION OF THE INVENTION

Figure 3:
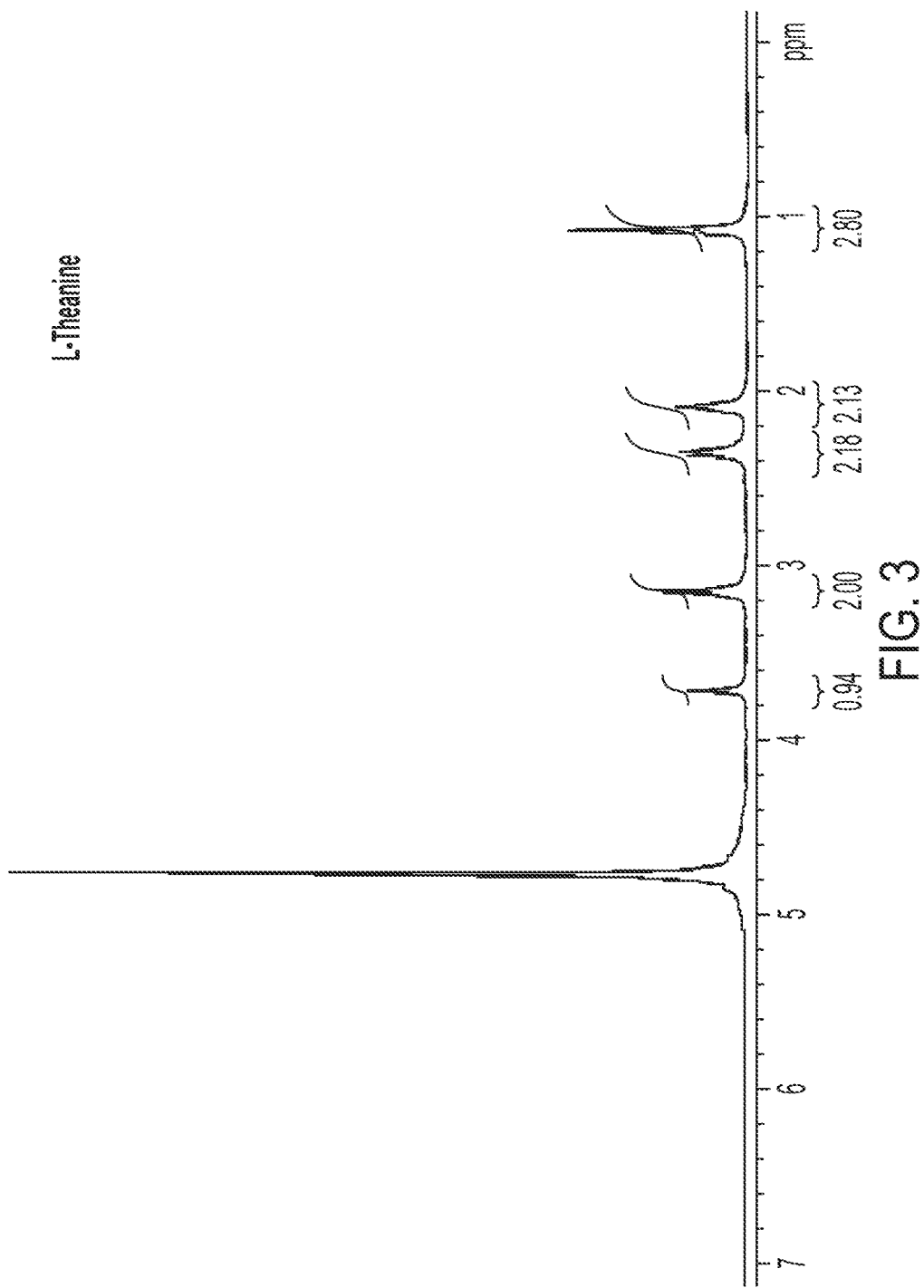
FIG. 3 is a depiction of the Nuclear Magnetic Resonance (NMR) spectrum of L-theanine.

The terminology used in the description presented herein is not intended to be interpreted in any limited or restrictive manner, simply because it is being utilized in conjunction with a detailed description of certain specific embodiments described herein. Furthermore, embodiments described herein can include several novel features, no single one of which is solely responsible for its desirable attributes or which is essential to practicing the embodiments described herein.

The term "formulation" or "composition" refers to preparations which are in such a form as to permit the biological activity of the active ingredients to be effective, and, therefore may be administered to a subject for the claimed and described use.

Unless otherwise specified herein, an "effective amount" as used herein includes within its meaning a non-toxic but sufficient amount of a compound active ingredient or composition comprising the same for use in the embodiments disclosed herein to provide the desired biological effect. Similarly "an amount effective to" as used herein includes within its meaning a non-toxic but sufficient amount of a compound active ingredient or composition comprising the same to provide the desired effect. The exact amount of the active ingredient disclosed herein required will vary from subject to subject depending on factors such as the species being administered to, the age and general condition of the subject, the severity of the condition being addressed, the particular agent being administered, the weight of the subject, and the mode of administration and so forth. Thus, it is not possible to specify an exact "effective amount." However, for any given case, an appropriate "effective amount" may be determined by one of ordinary skill in the art using only routine methods. In some aspects, a therapeutically effective amount may include a dosing regimen.

When describing nutraceuticals, nutritional supplements, and dietary supplements, these terms are to be interpreted in the manner that would be given to them by the skilled artisan and in consideration of the guidelines of the U.S. Food and Drug Administration. Nutraceutical and dietary supplement compositions described herein may also include ingredients or components that are defined as generally recognized as safe (GRAS).

As used herein, the term "excipient material" refers to any compound that is part of a formulation that is not an active ingredient, i.e., one that has no relevant biological activity, and which is added to the formulation to provide specific characteristics to the dosage form, including by way of example, providing protection to the active ingredient from chemical degradation, facilitating release of a tablet or caplet from equipment in which it is formed, and so forth.

For oral administration, the compositions disclosed herein can be provided as a tablet, aqueous or oil suspension, dispersible powder or granule, emulsion, hard or soft capsule, syrup, elixir, or beverage. Solid dosage forms such as tablets and capsules may comprise an enteric coating. Compositions intended for oral use can be prepared according to any method known in the art for the manufacture of pharmaceutically acceptable compositions and such compositions may include one or more of the following agents: sweeteners, flavoring agents, coloring agents, coatings, and preservatives. The sweetening and flavoring agents will increase the palatability of the preparation. Tablets containing the complexes in admixture with non-toxic pharmaceutically acceptable excipients suitable for tablet manufacture are acceptable. Pharmaceutically acceptable vehicles such as excipients are compatible with the other ingredients of the formulation (as well as non-injurious to the patient). Such excipients include inert diluents such as calcium carbonate, sodium carbonate, lactose, calcium phosphate or sodium phosphate; granulating and disintegrating agents, such as corn starch or alginic acid; binding agents such as starch, gelatin or acacia; and lubricating agents such as magnesium stearate, stearic acid or talc. Tablets can be uncoated or can be coated by known techniques to delay disintegration and absorption in the gastrointestinal tract and thereby provide a sustained action over a longer period of time. For example, a time delay material such as glyceryl monostearate or glyceryl distearate alone or with a wax can be employed.

Formulations for oral use can also be presented as hard gelatin or non-gelatin capsules wherein the active ingredient is mixed with an inert solid diluent, for example calcium carbonate, calcium phosphate or kaolin, or as soft gelatin capsules wherein the active ingredient is mixed with water or an oil medium, such as peanut oil, liquid paraffin or olive oil. Aqueous suspensions can contain the complex of the invention in admixture with excipients suitable for the manufacture of aqueous suspensions. Such excipients include suspending agents, dispersing or wetting agents, one or more preservatives, one or more coloring agents, one or more flavoring agents and one or more sweetening agents such as sucrose or saccharin.

Oil suspensions can be formulated by suspending the active ingredient in a vegetable oil, such as arachis oil, olive oil, sesame oil or coconut oil, or in a mineral oil such as liquid paraffin. The oil suspension can contain a thickening agent, such as beeswax, hard paraffin or cetyl alcohol. Sweetening agents, such as those set forth above, and flavoring agents can be added to provide a palatable oral preparation. These compositions can be preserved by an added antioxidant such as ascorbic acid. Dispersible powders and granules of the invention suitable for preparation of an aqueous suspension by the addition of water provide the active ingredient in admixture with a dispersing or wetting agent, a suspending agent, and one or more preservatives. Additional excipients, for example sweetening, flavoring and coloring agents, can also be present.

Syrups and elixirs can be formulated with sweetening agents, such as glycerol, sorbitol or sucrose. Such formulations can also contain a demulcent, a preservative, a flavoring or a coloring agent.

It will be appreciated that the amount of the composition may be combined with a carrier material to produce a single dosage form. Such forms will vary depending upon the host treated and the particular mode of administration.

Aqueous suspensions may contain the composition disclosed herein in admixture with excipients suitable for the manufacture of aqueous suspensions. Such excipients include suspending agents, dispersing or wetting agents, one or more preservatives, one or more coloring agents, one or more flavoring agents and one or more sweetening agents such as sucrose or saccharin.

Controlled release vehicles are well known to those of skill in the pharmaceutical sciences. The technology and products in this art are variably referred to as controlled release, sustained release, prolonged action, depot, repository, delayed action, retarded release and timed release; the words "controlled release" as used herein is intended to incorporate each of the foregoing technologies.

Numerous controlled release vehicles are known, including biodegradable or bioerodable polymers such as polylactic acid, polyglycolic acid, and regenerated collagen. Known controlled release drug delivery devices include creams, lotions, tablets, capsules, gels, microspheres, liposomes, ocular inserts, minipumps, and other infusion devices such as pumps and syringes. Implantable or injectable polymer matrices, and transdermal formulations, from which active ingredients are slowly released, are also well known and can be used in the disclosed methods.

Controlled release preparations can be achieved by the use of polymers to form complexes with or absorb the composition. The controlled delivery can be exercised by selecting appropriate macromolecules such as polyesters, polyamino acids, polyvinylpyrrolidone, ethylenevinyl acetate, methylcellulose, carboxymethylcellulose, and protamine sulfate, and the concentration of these macromolecule as well as the methods of incorporation are selected in order to control release of active complex.

Controlled release of active complexes can be taken to mean any of the extended release dosage forms. The following terms may be considered to be substantially equivalent to controlled release, for the purposes of the present disclosure: continuous release, controlled release, delayed release, depot, gradual release, long term release, programmed release, prolonged release, programmed release, proportionate release, protracted release, repository, retard, slow release, spaced release, sustained release, time coat, time release, delayed action, extended action, layered time action, long acting, prolonged action, sustained action medications and extended release, release in terms of pH level in the gut and intestine, breakdown of the molecule and based on the absorption and bioavailability.

Hydrogels, wherein the composition is dissolved in an aqueous constituent to gradually release over time, can be prepared by copolymerization of hydrophilic mono-olefinic monomers such as ethylene glycol methacrylate. Matrix devices, wherein the composition is dispersed in a matrix of carrier material, can be used. The carrier can be porous, non-porous, solid, semi-solid, permeable or impermeable. Alternatively, a device comprising a central reservoir of magnesium picolinate surrounded by a rate controlling membrane can be used to control the release of the complex. Rate controlling membranes include ethylene-vinyl acetate copolymer or butylene terephthalate/polytetramethylene ether terephthalate. Use of silicon rubber depots is also contemplated.

Controlled release oral formulations are also well known. In one embodiment, the composition is incorporated into a soluble or erodible matrix, such as a pill or a lozenge. In another example, the oral formulations can be a liquid used for sublingual administration. These liquid compositions can also be in the form a gel or a paste. Hydrophilic gums, such as hydroxymethylcellulose, are commonly used. A lubricating agent such as magnesium stearate, stearic acid, or calcium stearate can be used to aid in the tableting process.

Provided herein are compounds, compositions, methods of making and using compounds and compositions for enhancing the quality and benefits of sleep and/or wakefulness. As discussed herein, a novel magnesium di-L-theanate is provided for use in enhancing the quality and benefits of sleep and/or wakefulness. A proffered structure of the novel magnesium di-L-theanate of the invention is:

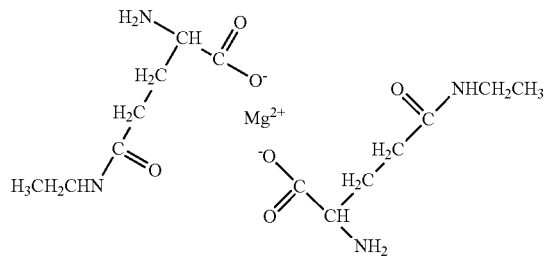

There are important attributes or characteristics of sleep that are relevant to the invention. Some of those attributes or characteristics are discussed herein.

As seen in Tables 1 and 2, different forms of theanine can exhibit differing physiological effects on a subject, including brain neurotransmitter levels and the antioxidant status within the brain.

TABLE 1

The effect of different forms of theanine on levels of brain serotonin, dopamine and melatonin in caffeine-induced wakefulness mice

| Analyte | Control | C | CT | CMgT1 | CMgT2 | P* |
|---|---|---|---|---|---|---|
| Serotonin, ng/g | $836.29 + 44.21_a$ | $571.00 + 42.14_d$ | $655.43 + 35.46_c$ | $762.29 + 25.34_b$ | $751.43 + 30.34_b$ | 0.0001 |
| Dopamine, ng/g | $968.00 + 74.44_a$ | $584.86 + 72.47_d$ | $779.00 + 77.73_c$ | $832.71 + 74.50_{bc}$ | $895.57 + 61.93_{ab}$ | 0.0001 |
| Melatonin, pg/g | $0.95 + 0.07_a$ | $0.59 + 0.05_a$ | $0.69 + 0.08_c$ | $0.80 + 0.03_b$ | $0.85 + 0.04_b$ | 0.0001 |

C: Caffeine; T: Theanine: Mg: Magnesium; MgT: Magnesium theanate.

Data are presented as means and standard deviations.

$^{a-c}$Means in the same line without a common subscript differ significantly ($P < 0.05$; *ANOVA and Turkey's post-hoc test).

The assays were performed by ELISA.

TABLE 2

The effect of different forms of theanine on brain antioxidant status in caffeine-induced wakefulness mice.

| Analyte | Control | C | CT | CMgT1 | CMgT2 | P* |
|---|---|---|---|---|---|---|
| MDA, nmol/g | $1.71 + 0.11_a$ | $2.83 + 0.13_a$ | $2.46 + 0.17_b$ | $2.24 + 0.14_c$ | $2.24 + 0.09_c$ | 0.0001 |
| SOD, IU/mg protein | $161.29 + 7.09_a$ | $89.00 + 5.16_a$ | $117.14 + 13.89_c$ | $131.14 + 9.86_b$ | $137.29 + 5.99_b$ | 0.0001 |
| CAT, IU/mg protein | $43.53 + 4.91_a$ | $24.40 + 1.62_a$ | $29.51 + 2.06_c$ | $36.47 + 1.27_b$ | $35.96 + 2.52_b$ | 0.0001 |
| GSHPx, IU/mg protein | $21.24 + 4.28_a$ | $12.07 + 2.89_b$ | $15.56 + 7.94_{ab}$ | $17.743.25_{ab}$ | $19.11 + 2.39_{ab}$ | 0.009 |

C: Caffeine; T: Theanine: Mg: Magnesium; MgT: Magnesium theanate; MDA: Malondialdehyde; SOD: Super Oxide Dismutase; CAT: Catalase: GSPHx: Gluthatione Peroxidase.
Data are presented as means and standard deviations.
$^{a-c}$Means in the same line without a common subscript differ significantly ($P < 0.05$; *ANOVA and Turkey's post-hoc test).

The terminology used in the description presented herein is not intended to be interpreted in any limited or restrictive manner, simply because it is being utilized in conjunction with a detailed description of certain specific embodiments described herein. Furthermore, embodiments described herein can include several novel features, no single one of which is solely responsible for its desirable attributes or which is essential to practicing the embodiments described herein.

L-Theanine is a common name for the chemical 2-amino-4-(ethylcarbamoyl)-butyric acid, a chiral compound that exists in the L-(S)-enantiomeric form in nature. L-Theanine is certified as Generally Recognized as Safe (GRAS) for use by the U.S. Food and Drug Administration.

The term "magnesium" refers to the magnesium cation, $Mg^{2+}$.

"Umami" means delicious, savory, broth-like or meaty flavor and has been accepted as the fifth taste in addition to sweet, salt, sour and bitter. The umami taste has characteristic qualities that differentiate it from other tastes, including a taste-enhancing synergism between two umami compounds and a prolonged aftertaste. Biochemically, various G-protein coupled receptors (such as truncated type 1 and 4 metabotropic glutamate receptors in the oral cavity) contain heterodimer T1R1 and T1R3 subreceptors that respond specifically to umami stimuli.

As used herein, "identifying," refers to detecting or selecting a subject from a population of potential subjects, for example, to establish that a particular subject possesses certain properties or characteristics. "Identifying" may include, for example, self-identification, self-diagnosis, and diagnosis by a medical professional.

As used herein, "treat," "treatment," or "treating," refers to administering or providing a composition for prophylactic and/or therapeutic purposes.

As used herein, the terms "prophylactic treatment," "prevent," or "preventing," refer to treating a subject who does not yet exhibit symptoms of a disease or condition, but who is susceptible to, or otherwise at risk of, a particular disease or condition, whereby the treatment reduces the likelihood that the patient will develop the disease or condition. A "disorder" is any condition that would benefit from treatment with the compositions described herein.

As used in the claims below and throughout this disclosure, the phrase "consisting essentially of" is meant including any elements listed after the phrase, and limited to other elements that do not interfere with or contribute to the activity or action specified in the disclosure for the listed elements. Thus, the phrase "consisting essentially of" indicates that the listed elements are required or mandatory, but that other elements are optional and can or cannot be present depending upon whether or not they affect the activity or action of the listed elements. For example, the use of a composition "consisting essentially of magnesium di-L-theanate" for the treatment of a particular disease or disorder would exclude other ingredients that were known to be active in combating the particular disease or disorder.

As used herein, a composition that "substantially" comprises a compound means that the composition contains more than about 80% by weight, more preferably more than about 90% by weight, even more preferably more than about 95% by weight, and most preferably more than about 98% by weight of the compound.

The term "about," unless otherwise stated explicitly herein, means±20%. For instance about 100 means 80 to 120, about 5 means 4 to 6, about 0.3 means 0.24 to 0.36, and about 60% means 48% to 72% (not 40% to 80%).

The term "pharmaceutical formulation" refers to preparations which are in such a form as to permit the biological activity of the active ingredients to be effective, and, therefore may be administered to a subject for therapeutic use.

A "therapeutically effective amount" as used herein includes within its meaning a non-toxic but sufficient amount of a compound active ingredient or composition comprising the same for use in the embodiments disclosed herein to provide the desired therapeutic effect. Similarly "an amount effective to" as used herein includes within its meaning a non-toxic but sufficient amount of a compound active ingredient or composition comprising the same to provide the desired effect. The exact amount of the active ingredient disclosed herein required will vary from subject to subject depending on factors such as the species being treated, the age and general condition of the subject, the severity of the condition being treated, the particular agent being administered, the weight of the subject, and the mode of administration and so forth. Thus, it is not possible to specify an exact "effective amount." However, for any given case, an appropriate "effective amount" may be determined by one of ordinary skill in the art using only routine methods. In some aspects, a therapeutically effective amount may include a dosing regimen. For example, a therapeutically effective amount may include about 1 mg of magnesium di-L-theanate orally consumed each day for fourteen consecutive days. In some aspects, a therapeutically effective amount may include about 1 mg of magnesium di-L-theanate orally consumed each day for thirty consecutive days. Compositions including magnesium di-L-theanate may include, for example, between 0.1-10 grams of magnesium di-L-theanate.

In addition, the appropriate dosage of the compositions will depend, for example, on the condition to be treated, the severity and course of the condition, whether the composition is administered for preventive or therapeutic purposes, previous therapy, the patient's clinical history and response to the composition, the type of composition used, and the discretion of the attending physician. The composition is suitably administered to the subject at one time or over a series of treatments and may be administered to the patient at any time from diagnosis onwards. The composition may be administered as the sole treatment or in conjunction with other drugs or therapies useful in treating the condition in question.

Biochemical Actions of L-Theanine. Biochemically, L-theanine is a structural analogue of L-glutamate, the most important excitatory neurotransmitter of mammalian nervous systems. Recent studies suggest that L-theanine exerts neuroprotective effects by binding to and blocking glutamate receptors in the central nervous system, thus reducing excitatory impulses and lowering the stimulatory effects of glutamate. L-Theanine has been reported to stimulate production of neurotransmitters such as serotonin, dopamine, and 7-aminobutyric acid (GABA) in the brain. Through stimulation of the production of alpha waves in the brain, L-theanine has been reported to create a state of deep relaxation, wakefulness, and mental alertness. (U.S. Pat. No. 10,335,384) In U.S. Pat. No. 5,501,866 Kakuda et al. disclosed that L-theanine and/or a substance having theanine for its major active ingredient was able to inhibit the stimulatory action of caffeine without degrading taste-related qualities of caffeine-containing beverages and foods. In U.S. Pat. No. 10,449,148, Gutierrez and Beer stated that compositions comprising inositol, N-acetyl L-tyrosine, pyrroloquinoline quinone, choline bitartrate, L-theanine, and acetyl L-carnitine can be used, in both solid and liquid forms, to improve brain health. Likewise, in U.S. Patent Application No. 2015/0320814, Patel et al. stated that compositions comprising combinations of niacin, magnesium, ashwagandha, passionflower, skullcap, St. John's Wort, gamma-aminobutyric acid, chamomile, and L-theanine are useful for treating anxiety and depression. In U.S. Patent Application No. 2002/0122835, Bucci et al. stated that compositions comprising zinc, magnesium, and vitamin B6, optionally including theanine, are effective for enhancing muscle and tissue recovery during sleep following intense physical exercise.

Following oral administration, Nathan reported that L-theanine is absorbed from the intestine and crosses the blood-brain barrier within 30 minutes of administration. [17] Theanine's actions include striatal dopamine release following stimulation of NMDA receptors, as well as induction of significant increases in serotonin in the striatum, hippocampus, and hypothalamus. Observation that theanine prevented ischemic neural death in field CA1 of gerbil hippocampus suggests that this amino acid derivative may play a role in neuroprotection.

With respect to effects on the sleep cycle, Jang et al. reported that rodents receiving L-theanine exhibit a U-shaped dose response profile. [11] Doses of 20 mg/kg significantly and beneficially altered the sleep cycle, but both lower and higher doses of L-theanine were less effective. In the caffeine-induced wake mouse model, a dose of 20 mg/kg L-theanine was found to significantly decrease sleep latency and increase sleep time, including increases in REM time during the sleep cycle. Single doses of theanine had little effect on NREM time but chronic administration caused a significant increase in NREM time. The changes included an increase in theta waves and a decrease in delta waves during N1, followed by increases in delta waves during subsequent stages of NREM sleep.

Biochemical Actions of the Magnesium Ion. Following oral administration, the magnesium ion is absorbed from the intestine via both paracellular and transcellular transport mechanisms. Since both mechanisms depend on the concentration of soluble magnesium ion, more soluble organic magnesium compounds are better absorbed than less soluble inorganic compounds. In addition, the composition of the organic magnesium compound has significant effects on absorption and bioavailability of magnesium. Ates et al. reported that organic acid magnesium compounds (e.g., magnesium citrate and magnesium malate) were more poorly absorbed than certain magnesium complexes with amino acids. [2] Even in this latter category, dose- and structure-dependent differences in absorption were found. For example, magnesium acetyl taurate exhibited significantly better absorption and bioavailability than magnesium glycinate.

The magnesium cation ($Mg^{2+}$) plays important roles in the neural system. It competes with calcium ($Ca^{2+}$) to mediate N-methyl-D-aspartic acid receptor (NMDAR)-dependent neural responses to excitatory amino acids, inhibit calcium channels, calcium influx, and glutamate release. (Inhibition of glutamate release is particularly important during the sleep latency period, since glutamate transporters mediate synchronized elevation of L-glutamate, activity which efficiently downregulates melatonin secretion in the pineal gland.) [14] This cation stabilizes cell membranes. Magnesium deficiency results in increased free radicals production, increased oxidative damage to tissues and metabolites, increased superoxide anion production by inflammatory cells, decreased antioxidant enzyme expression and activity, decreased cellular and tissue antioxidant levels, and increased peroxide production. Magnesium insufficiency produces vasospasm, whereas elevated magnesium induces tone relaxation in cerebral arteries.

A recent double-blind randomized clinical trial was conducted in 46 elderly subjects, randomly allocated into the (supplemental) magnesium or the placebo group.[1] No significant differences were observed in assessed variables between the two groups at baseline. After 8 weeks of daily supplementation with 500 mg magnesium, as compared to the placebo group, the magnesium-supplemented group exhibited statistically significant increases in sleep time ($P=0.002$), sleep efficiency ($P=0.03$), concentration of serum renin ($P<0.001$), and concentration of melatonin ($P=0.007$). Early morning wakening time of the magnesium-supplemented group was also shortened. Insomnia Severity Index scores, a subjective measure, also improved.

Recently, Ding et al. reported that magnesium is one of three major extracellular ions that control the state-dependent patterns of neural activity. [5] In general, Ding et al. found that as rodents transitioned from sleep to wakefulness, the extracellular concentrations of the hydrogen ion, magnesium and calcium decreased over a span of about a minute, while the concentration of extracellular potassium increased rapidly. In addition, the extracellular space volume decreased. These changes were accompanied by increased EEG amplitude and delta wave prevalence and increased EMG activity. Conversely, as the rodents transitioned from wakefulness to sleep, extracellular space volume increased by about 30%. The volume increase was accompanied by relatively slow increases in the extracellular concentrations of the hydrogen ion, magnesium, and calcium and rapid decreases in the concentration of extracellular potassium.

The changes in magnesium ion concentration with sleep reported by Ding et al. also correlate strongly with reports that magnesium supplementation may have profoundly beneficial effects on cognition and memory. [5] The increase in extracellular volume and the relatively slow increase in extracellular magnesium resulting from transition to sleep strongly associate with magnesium's large sphere of hydration and the ion's ability to bind to ATP, respectively. (Magnesium binding to ATP facilitates its passage through cell membranes into the extracellular space. [10]) The changes in ion concentration during sleep also gain support from a report by Coskuner and Murray that ATP binding to amyloid-β (Aβ) protein inhibits misfolding, thus protecting against Aβ-fiber mediated cytotoxicity.[3] The inhibition is enhanced by magnesium.

Experiments

Data obtained in two experiments using widely used rodent models of sleep showed that administration of a magnesium di-L-theanate composition, the magnesium complex of L-theanine, caused sleep and wakefulness responses in the animals that were significantly and beneficially different from those of L-theanine, including differences from results expected following administration of mixtures of L-theanine and magnesium salts.

Experiments using the caffeine-induced "awake" mouse model (which are described in greater detail in Example 5 and illustrated in FIGS. 7-11 showed a number of significant differences between the actions in the brain of conventional L-theanine and those of magnesium di-L-theanate compositions of the invention following metabolic disruption by caffeine (Table 3 in Example 5). The differences included:

1. A significant decrease in the sleep latency period caused by magnesium di-L-theanate compositions as compared to L-theanine itself. This decrease indicates that magnesium di-L-theanate compositions are more effective than theanine in reducing the excitatory effects of caffeine in the brain.

2. A significant lengthening and normalization of sleep duration caused by magnesium di-L-theanate compositions as compared to L-theanine itself. This normalization indicates that magnesium di-L-theanate compositions act more effectively than theanine to normalize sleep cycles and sleep time.

3. A significant increase in the number of animals falling asleep in the magnesium di-L-theanate groups as compared to the L-theanine-treated animals.

4. A significant increase in the amplitude of brain waves induced by magnesium di-L-theanate compositions as compared to L-theanine itself. This increase, which was maintained throughout the 120 minute study period, was accompanied by a significant reduction in spike frequency of electrical activity in the brain. These changes indicate that magnesium di-L-theanate compositions act more effectively than theanine in inducing slow wave sleep, relatively uninterrupted by disruptive brain activity (spikes) associated with wakefulness.

5. A significant restoration in the concentration of key neurotransmitters (brain serotonin, dopamine, and melatonin) as compared to L-theanine itself. This normalization indicates that the quality and benefits of sleep will be enhanced.

6. A decrease in oxidative stress and a restoration of brain anti-oxidant status caused by caffeine was induced by magnesium di-L-theanate compositions as compared to L-theanine itself. This normalization indicates that adverse effects of stress and metabolic disruption and oxidative stress will be moderated by magnesium di-L-theanate compositions.

7. A significant normalization of key indicators of brain cell survival after stress and apoptotic damage in the magnesium di-L-theanate groups as compared to L-theanine-treated animals. This action indicates that magnesium di-L-theanate compositions are neuroprotectants that can reasonably be expected to protect against tissue and functional damage in the brain.

8. A significant diminution in the caffeine-related reduction of GABA and other neurotransmitter receptors in the brain was induced by magnesium di-L-theanate compositions as compared to L-theanine itself. This induction indicates that magnesium di-L-theanate compositions can reasonably be expected to protect and support normal brain function, during both sleep and wakefulness.

Taken together, these data support the conclusion that administration of a magnesium di-L-theanate composition of the invention enhances the quality and duration of sleep by multiple mechanisms, including mechanisms which provide neuroprotection. The positive changes to the quality and duration of sleep are more beneficial than those elicited by theanine.

In addition, experiments using the pentobarbital-induced sleep test mouse model confirmed the results from the caffeine-induced wakefulness model. (These experiments are described in greater detail in Example 5.) In these experiments, either theanine (20 mg/kg) or magnesium di-L-theanate composition (20 mg theanine/kg) was administered orally to mice in test groups. Subsequently, pentobarbital was administered intraperitoneally to induce a hypnotic state that promoted sleep. The effects on sleep of the test agents were monitored.

Experimental data showed that administration of theanine or magnesium di-L-theanate composition significantly reduced the sleep latency period and significantly increased the duration of sleep. About 62% of the animals receiving L-theanine failed to sleep during the pre-defined 10-minute period following pentobarbital administration. Surprisingly, over 50% of the animals receiving magnesium di-L-theanate compositions fell asleep. Thus, by every measure that was monitored, treatment with a magnesium di-L-theanate composition was more effective than treatment with theanine.

Magnesium di-L-theanate Compositions. Magnesium di-L-theanate compositions of the invention contain 5.5-6.0% magnesium by weight and 94.0-94.5% L-theanate by weight. Magnesium di-L-theanate exhibits an optical rotation of 34°, different from that of L-theanine (7.7-8.5°). The compositions are stable during storage under conditions having temperatures ranging from −80° C. to +120° C. at low relative humidity. Storage stability is greatest at temperatures from −80° C. to +60° C. at low relative humidity. Storage at higher temperatures or elevated humidity is tolerated only for short periods of time. The compositions exhibit a solubility in water of about 650 mg/mL.

The differences in optical rotation of magnesium di-L-theanate and L-theanine confirm that the compositions of the invention are not simply mixtures of magnesium ion and L-theanine. A simple mixture would continue to exhibit the optical rotation of L-theanine (7.7-8.5°) or a near value. Compositions of the invention have significantly lower optical rotations of 34°.

All of these features of the compositions of the invention support their use as compositions to enhance the quality and benefits of sleep. The storage stability of the compositions enables facile formulation in a variety of solid or semi-solid dosage forms intended for oral administration. Likewise, the solubility in water and stability of the compositions in aqueous solutions enable formulation in liquid dosage forms intended for oral, intravenous, or peritoneal administration. Liquid dosage forms (as well as liquid dosage forms prepared from magnesium di-L-theanate compositions in the solid state) have the advantages that administration of liquids to infants, children, the elderly, and subjects having difficulty swallowing (dysphagia) is easier than administration of solid dosage forms.

Moreover, solutions of compositions of the invention are characterized by an absence of bitter or umami taste. As Lawless et al. reported, magnesium salts are typically characterized by complex tastes (umami). [16] Often the taste of a magnesium salt is described as bitter or as a combination of salty or sour tastes with lingering bitter aftertaste. These repugnant tastes typically increase with the concentration of magnesium salt. In contrast, both solid forms and solutions of compositions of the invention exhibit either a slightly sweet taste without aftertaste or an absence of taste. This presents an advantage, since subjects who imbibe bitter or salty compositions fail to repeat use of such compositions as prescribed or as indicated on product labels.

An oral dose of 20 mg L-theanine/kg of body weight is known to effectively reduce sleep latency and increase sleep duration in rodents. A dose of 500 mg magnesium (about 8 mg/kg body weight), administered daily for 8 weeks, is known to improve subjective measures of insomnia such as ISI score, sleep efficiency, sleep time and sleep onset latency, and early morning awakening in elderly people. Surprisingly, provision of about a milligram of magnesium, delivered to the brain concurrently with L-theanine as a magnesium di-L-theanate complex, was effective in reducing sleep latency, increasing sleep duration, and reducing (caffeine-related) metabolic disruption in the brain.

Experimental data (Example 5) showed that following administration, magnesium di-L-theanate compositions were rapidly absorbed and distributed to the brain, where the compositions acted to induce and maintain sleep via normal physiological mechanisms. No side effects were observed during or after treatment. No adverse effects were observed on activities during or immediately after wakefulness. Neither component in magnesium di-L-theanate compositions of the invention (i.e., magnesium or L-theanine) has been reported to cause addiction.

Experimental data showed that as early as about 30 minutes after administration, magnesium di-L-theanate compositions exhibited beneficial enhancement of a spectrum of properties of sleep. Moreover, experimental data show that these effects were exhibited concurrently. The data did not show the effects of one ion during one period and effects of second ion at a different time, as would be expected if mixtures of theanine and magnesium were administered orally.

Briefly summarized, magnesium di-L-theanate compositions of the invention exhibited effective enhancement of sleep quality and by extension, are reasonably expected to enhance benefits of sleep. For example, it is reasonable to anticipate that magnesium di-L-theanate compositions, through their beneficial actions on sleep, will cause beneficial enhancements to:

Consolidation of long-term memory.

The volume and movement of the lymphatic system of the brain, providing opportunities for removal of metabolic waste, including misfolded proteins and other toxins.

Higher cortical function and cognition, including attention to decision-making, ability to multi-task, and performance of tasks that rely on memory.

Creativity.

Physical health and longevity, particularly in adulthood.

Finally, numerous studies have linked severe stress to the development of major depressive disorders and suicidal behaviors. Chronic stress has been shown to induce prolonged high concentrations of the stress hormone cortisol and to cause severe oxidative damage to mitochondrial function and membrane lipids in the brain. Mitochondria play a key role in synaptic neurotransmitter signaling by providing ATP, mediating lipid and protein synthesis, buffering intracellular calcium, and regulating apoptotic and resilience pathways. Membrane lipids are essential to central nervous system function, because cholesterol, polyunsaturated fatty acids, and sphingolipids form lipid raft regions on the membrane that mediate neurotransmitter signaling through G-protein coupled receptors and ion channels. Data from the animal studies that are detailed in Example 5 demonstrate that magnesium di-L-theanate compositions provide significantly better support to the brain undergoing stress than does theanine, magnesium, or mixtures of magnesium and theanine.

REFERENCES

1. Abbasi B, Kimiagar M, Sadeghniiat K, Shirazi M M, Hedayati M, Rashidkhani B. The effect of magnesium supplementation on primary insomnia in elderly: A double-blind placebo-controlled clinical trial. J Res Med Sci. 2012 December; 17(12): 1161-9. PubMed PMID: 23853635; PubMed Central PMCID: PMC3703169.
2. Ates M, Kizildag S, Yuksel O, Hosgorler F, Yuce Z, Guvendi G, Kandis S, Karakilic A, Koc B, Uysal N. Dose-dependent absorption profile of different magnesium compounds. Biol Trace Elem Res. 2019 December; 192(2): 244-251.
3. Coskuner O, Murray I V. Adenosine triphosphate (ATP) reduces amyloid-O protein misfolding in vitro. J Alzheimers Dis. 2014; 41(2): 561-74. PubMed PMID: 24625803.
4. Deckert J, Gleiter C H. Adenosinergic psychopharmaceuticals?Trends Pharmacol Sci 1989; 10: 99-100.
5. Ding F, O'Donnell J, Xu Q, Kang N, Goldman N, Nedergaard M. Changes in the composition of brain interstitial ions control the sleep-wake cycle. Science 2016 Apr. 29; 352(6285): 550-5.
6. Dominguez L J, Barbagallo M. Nutritional prevention of cognitive decline and dementia. Acta Biomed. 2018 Jun. 7; 89(2): 276-290.
7. Hafner M, Stepanek M, Taylor J, Troxel W M, van Stolk C. Why sleep matters—the economic costs of insufficient sleep. A cross-country comparative analysis. RAND Corp., Santa Monica, CA; 2016.
8. Haskell C F, Kennedy D O, Milne A L, Wesnes K A, Scholey A B. The effects of L-theanine, caffeine and their combination on cognition and mood. Biol Psychol. 2008 February; 77(2): 113-22. PubMed PMID: 18006208.
9. Henderson T, Griffin D, Bledsoe D. Compositions comprising magnolia, phellodendron, theanine and/or whey protein. U.S. Pat. No. 10,355,384. Filed: Sep. 15, 2017. Issued: Jul. 2, 2019.
10. Jackson J F, Atkinson M R. The requirement for bivalent cations in formation of nicotinamide-adenine dinucleotide by nicotinamide mononucleotide adenylyltransferase of pig-liver nuclei. Biochem J. 1966 October; 101(1):208-13.
11. Jang H S, Jung J Y, Jang I S, Jang K H, Kim S H, Ha J H, Suk K, Lee M G. L-theanine partially counteracts caffeine-induced sleep disturbances in rats. Pharmacol Biochem Behav. 2012 April; 101(2): 217-21.
12. Jo K, Suh H J, Choi H S. Polygonatum sibiricum rhizome promotes sleep by regulating nonrapid eye movement and GABAergic/serotonergic receptors in rodent models. Biomed Pharmacother. 2018 September; 105: 167-175.
13. Kakuda T. Neuroprotective effects of theanine and its preventive effects on cognitive dysfunction. Pharmacol Res. 2011 August; 64(2): 162-8. PubMed PMID: 21477654.
14. Kim S, Jo K, Hong K B, Han S H, Suh H J. GABA and 1-theanine mixture decreases sleep latency and improves NREM sleep. Pharm Biol. 2019 December; 57(1): 65-73.
15. Kimura K, Ozeki M, Juneja L R, Ohira H. L-Theanine reduces psychological and physiological stress responses. Biol Psychol. 2007 January; 74(1): 39-45. PubMed PMID: 16930802.
16. Lawless H T, Rapacki F, Home J, Hayes A. The taste of calcium and magnesium salts and anionic modifications. Food Qual Prefer 2003; 14: 319-325.
17. Nathan P J, Lu K, Gray M, Oliver C. The neuropharmacology of L-theanine (N-ethyl-L-glutamine): a possible neuroprotective and cognitive enhancing agent. J Herb Pharmacother. 2006; 6(2): 21-30. PubMed PMID: 17182482.
18. NIH State-of-the-Science Conference Statement on manifestations and management of chronic insomnia in adults. NIH Consens State Sci Statements. 2005 Jun. 13-15; 22(2): 1-30. PubMed PMID: 17308547.
19. Paterson L M, Wilson S J, Nutt D J, Hutson P H, Ivarsson M. A translational, caffeine induced model of onset insomnia in rats and healthy volunteers. Psychopharmacology (Berlin) 2007; 191: 943-50.

20. Sharma E, Joshi R, Gulati A. 1-Theanine: An astounding *sui generis* integrant in tea. Food Chem. 2018 Mar. 1; 242: 601-610. PubMed PMID: 29037735.
21. Shinomiya K, Omichi J, Ohnishi R, Ito H, Yoshida T, Kamei C. Effects of chlorogenic acid and its metabolites on the sleep-wakefulness cycle in rats. Eur J Pharmacol 2004; 504: 185-9.
22. Xiong W, Liang Y, Li X, Liu G, Wang Z. Erythrocyte intracellular Mg(2+) concentration as an index of recognition and memory. Sci Rep. 2016 Jun. 2; 6: 26975. doi: 10.1038/srep26975. PubMed PMID: 27253451; PubMed Central PMCID: PMC4890594.

EXAMPLES

Example 1. Synthesis of Magnesium Di-L-Theanate Using Magnesium Ethoxide

Figure 4:
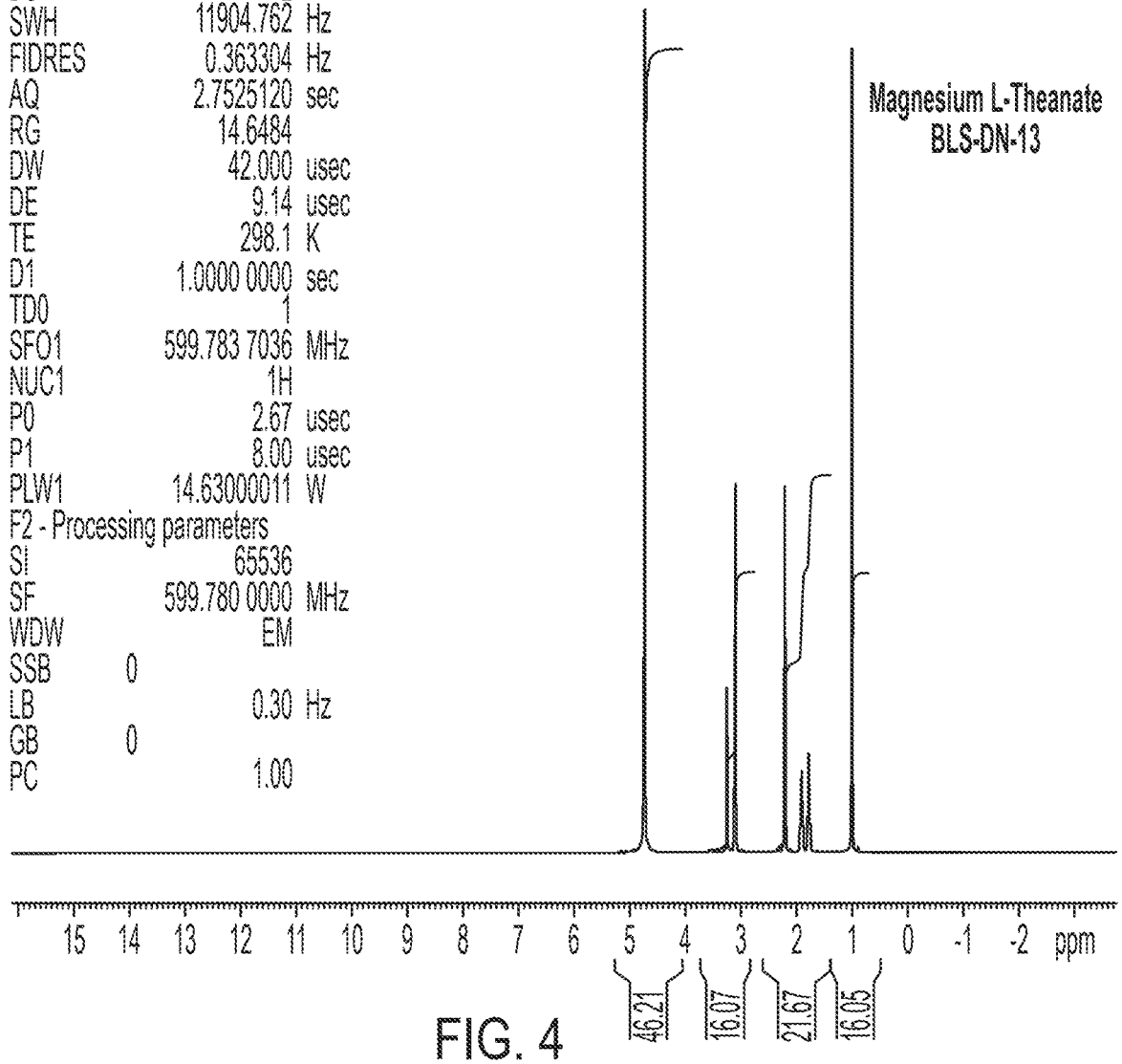
FIG. 4 is a depiction of the NMR spectrum of a magnesium di-L-theanate composition of the invention as made by Example 1 under EXAMPLES. Note the significant shifts in the absorptions as compared to the chemical shifts shown in FIG. 3 and the retention of all of the chemical shifts expected for theanine.

L-Theanine (87.1 g, 500 mmol) and magnesium ethoxide (28.6 g, 250 mmol) were slurried in 500 mL of absolute ethanol. The slurry was stirred and warmed as water (total 150 mL) was added in portions until a clear, yellow solution was obtained. The solution was cooled but no solid was obtained. The solution was concentrated to a solid by evaporation under vacuum. The solid was slurried with methanol to break up the bulk into fine particles. The slurry was filtered to isolate the product, a white solid. The product was slurried in 250 mL of hot ethanol and water was added until a solution was obtained. The yellow solution was treated with charcoal and filtered. The filtrate was concentrated to dryness and then further dried at 50° C. under vacuum to obtain a brittle solid. The solid was crushed into fine particles. About 92.6 g (100% of theoretical yield) of off-white magnesium di-L-theanate (Lot BLS-DN-13) was thus obtained. The $^1$H-NMR spectrum of magnesium di-L-theanate (FIG. 4) confirms that the salt was successfully prepared. A sample was submitted for magnesium analysis. The result confirmed that 5.80% by weight magnesium was present vs. a theoretical value of 5.97% by weight. This result indicates a purity of 97%. The product exhibited an optical rotation of 4°.

Example 2. Synthesis of Magnesium Di-L-Theanate Using Magnesium Ethoxide

L-Theanine (67 g, 386 mmol) and magnesium ethoxide (20 g, 175 mmol) were slurried in 300 mL of methanol and 30 mL of water. The slurry was stirred overnight. The next morning the reaction mixture had solidified. The solid was isolated by filtration and washed with acetone before air-drying. The solid was crushed into fine particles and dried further under vacuum. An amount (100% of theoretical yield) of off-white magnesium di-L-theanate (Lot AA-209-138) was thus obtained. The $^1$H-NMR spectrum of magnesium di-L-theanate confirms that the salt was successfully prepared. A sample was submitted for magnesium analysis. The result confirmed that 5.60% by weight magnesium was present vs. a theoretical value of 5.97% by weight. This result indicates a purity of 94%. The product exhibited an optical rotation of 3°.

Example 3. Synthesis of Magnesium Di-L-Theanate Using Magnesium Oxide

Figure 5:
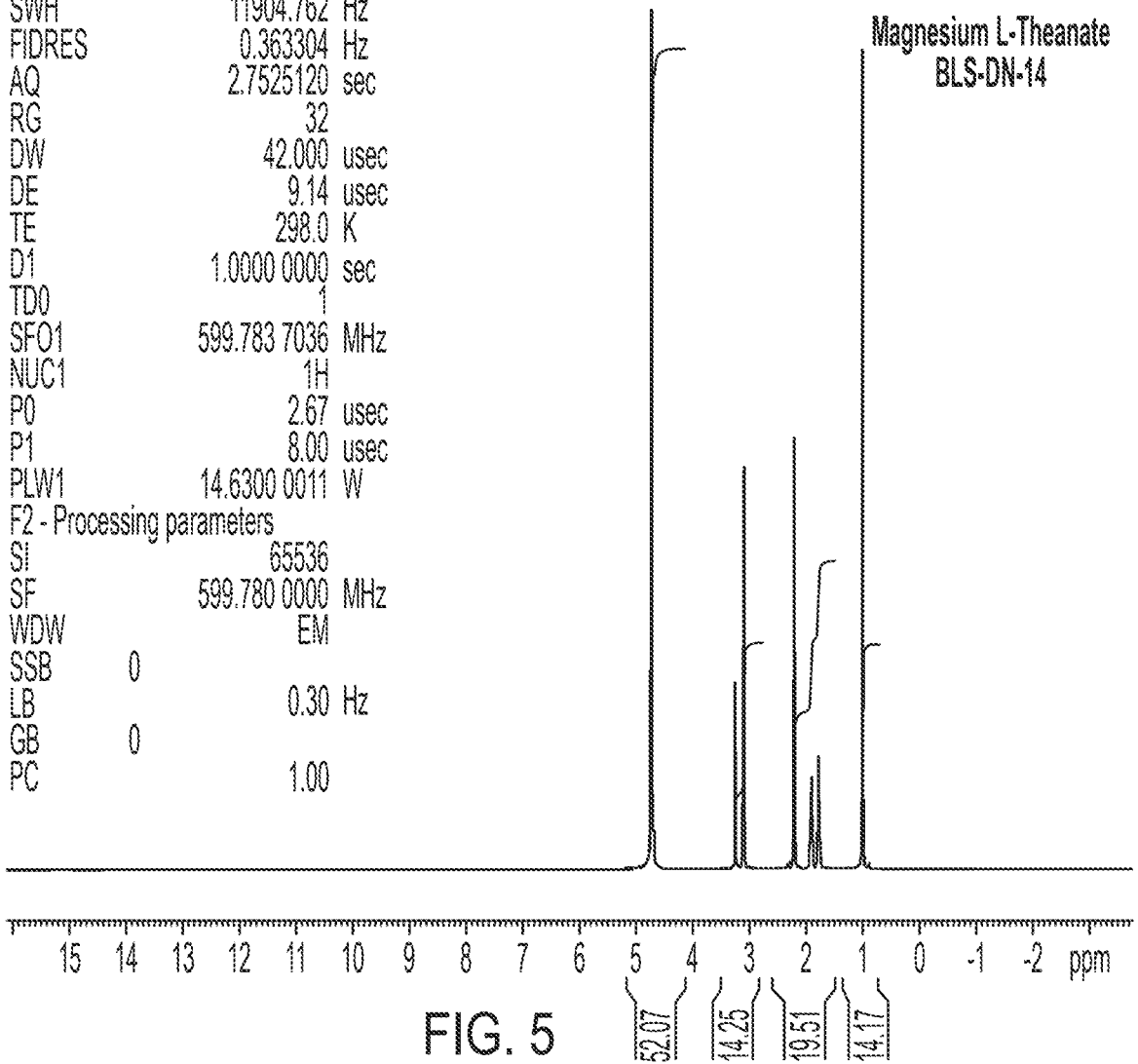
FIG. 5 is a depiction of the NMR spectrum of a magnesium di-L-theanate composition of the invention as made by Example 3 under EXAMPLES. Note the significant shifts in the absorptions as compared to the chemical shifts shown in FIG. 3 and the retention of all of the chemical shifts expected for theanine.

L-Theanine (4.4 g, 25 mmol) was dissolved 7 mL of water (the minimum volume needed to obtain a clear and colorless solution). Nanoparticulate magnesium oxide (0.5 g, 12.5 mmol) was added. The resulting slurry was stirred overnight. The next day the slurry had clarified significantly. To ensure that reaction was complete, the cloudy solution was warmed and stirred for 30 minutes. After cooling to ambient temperature, the cloudy solution was filtered. The filtrate was concentrated to dryness under vacuum to provide a white solid. The solid was dried at 50° C. under vacuum. The $^1$H-NMR spectrum of magnesium di-L-theanate (FIG. 5) confirms that the salt was successfully prepared. After drying at 50° C. under vacuum, a sample was submitted for magnesium analysis. The result confirmed that 5.52% by weight magnesium was present vs. a theoretical value of 5.97% by weight. This result suggests the product is 92% pure and may contain residual L-theanine. About 3.2 g (70% of theoretical yield) of white magnesium di-L-theanate was thus obtained.

Example 4. Synthesis of Magnesium Di-L-Theanate by Exchange Reaction

Figure 6:
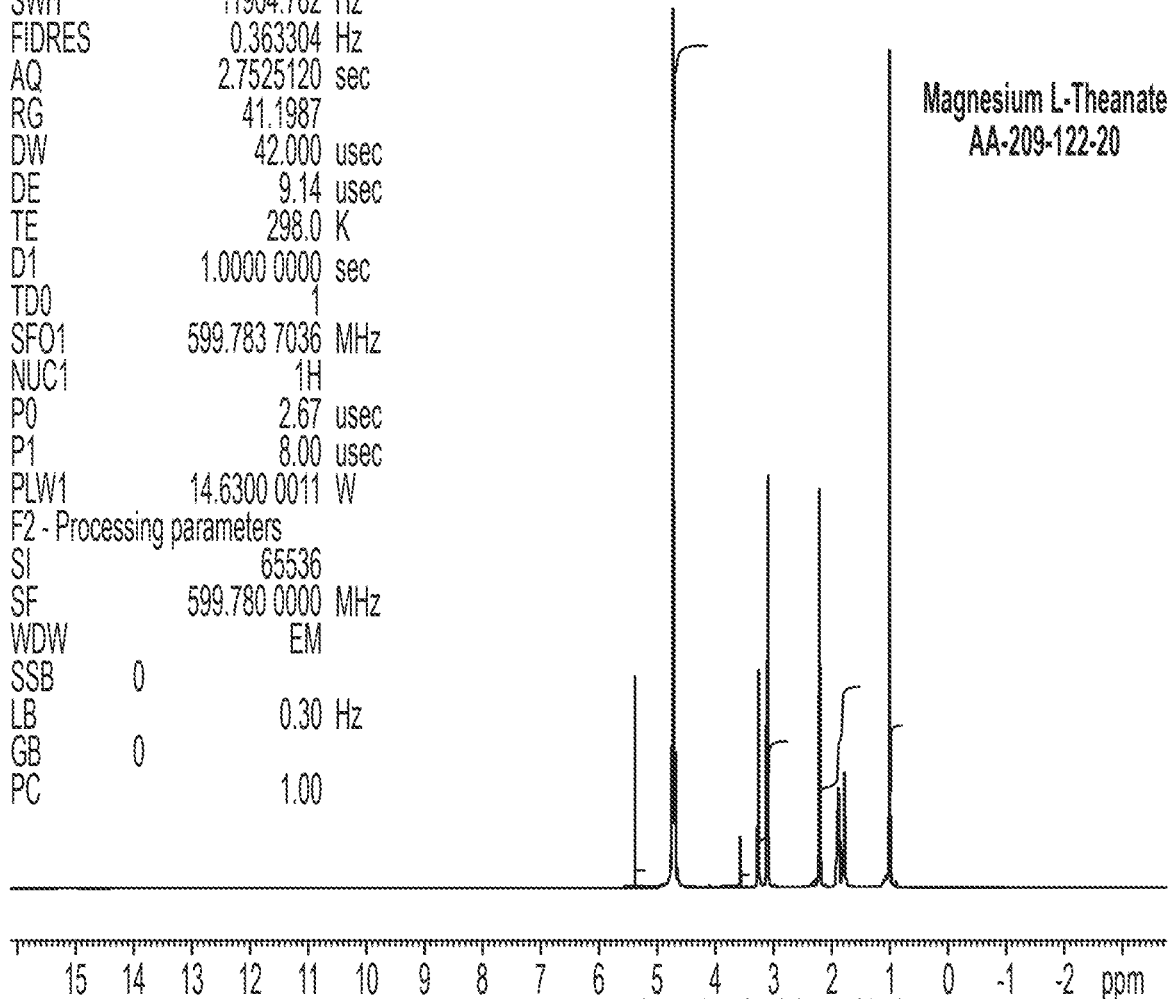
FIG. 6 is a depiction of the NMR spectrum of a magnesium di-L-theanate composition of the invention as made by Example 4 under EXAMPLES. Note the significant shifts in the absorptions as compared to the chemical shifts shown in FIG. 3 and the retention of all of the chemical shifts expected for theanine.
Figure 7A:
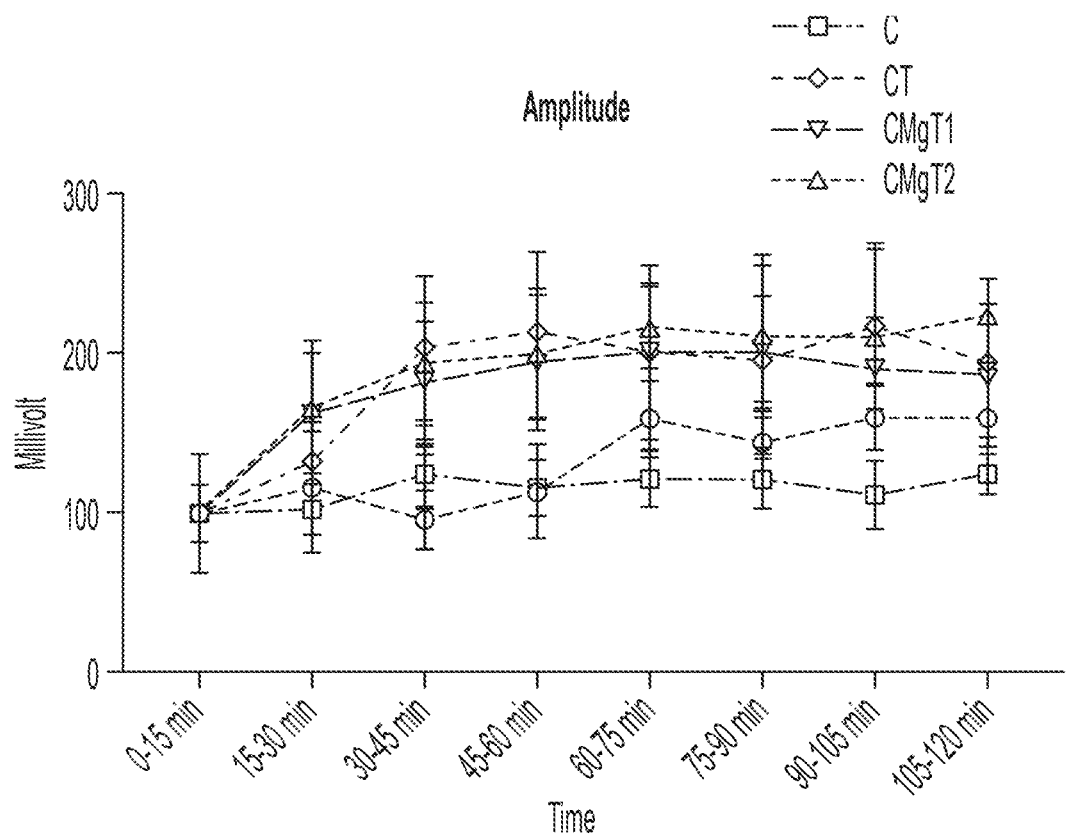
FIG. 7(A-B). Effect of different forms of theanine on amplitude (7A) and frequency (7B) in caffeine-induced wakefulness mice (Repeated Measure ANOVA and Turkey's post-hoc test).
Figure 7B:
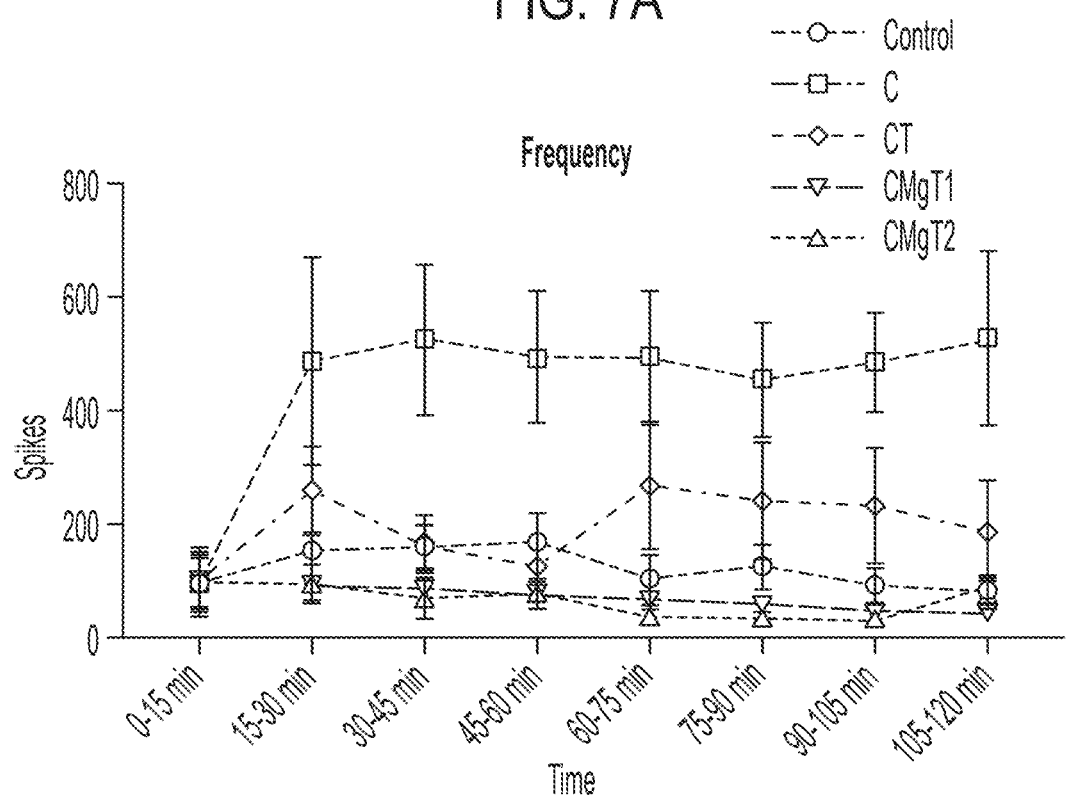
Figure 8A:
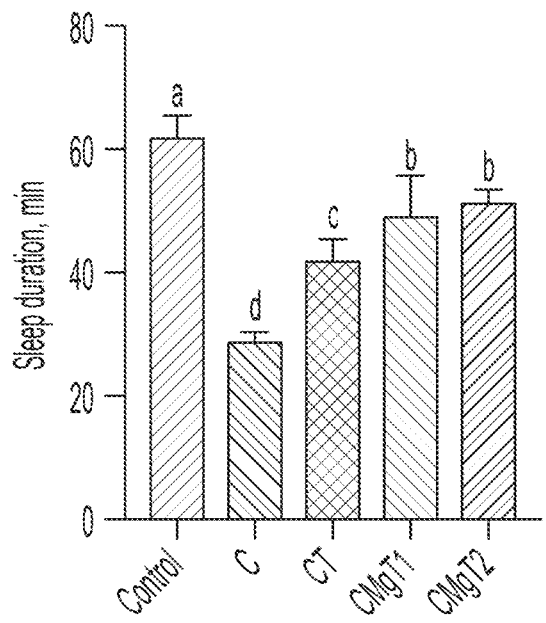
FIG. 8(A-C). Effect of different forms of theanine on sleep duration (8A), sleep latency (8B) and percent of number falling sleep (8C) in caffeine-induced wakefulness mice. Data are presented as a bar graph with means and standard deviations. a-e: Values within the bars with different subscripts are significantly different (ANOVA and Turkey's post-hoc test).
Figure 8B:
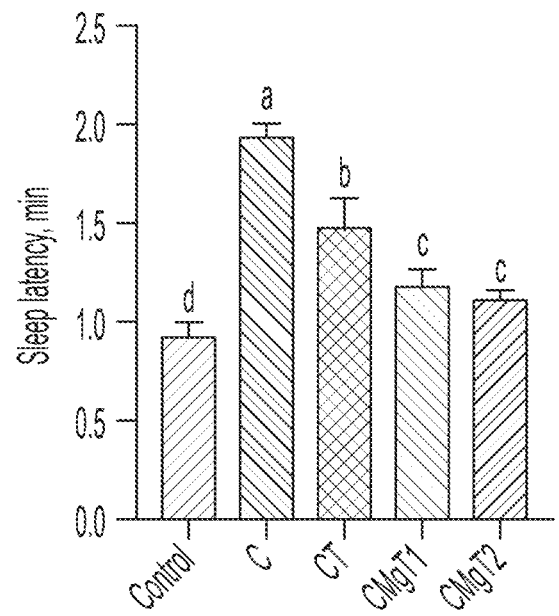
Figure 8C:
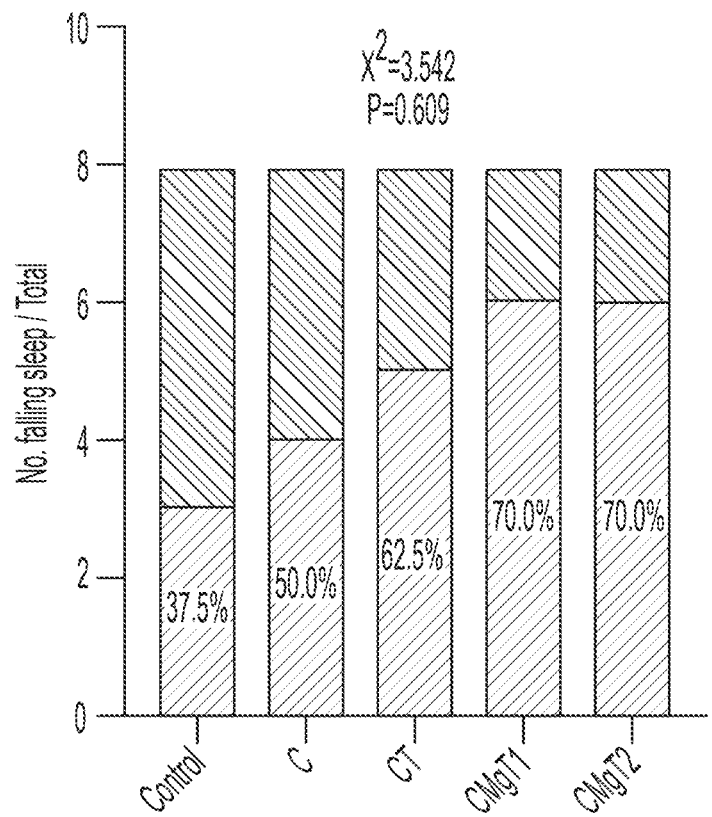
Figure 10A:
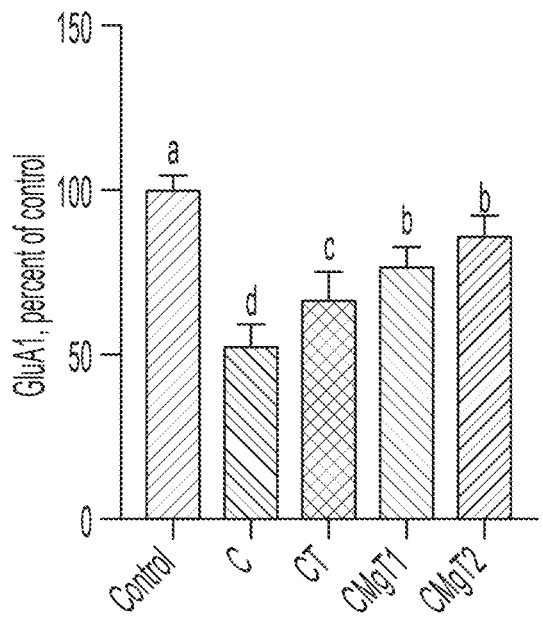
FIG. 10(A-D). Effect of different forms of theanine on GluA1 (10A), GluN1 (10B) and GluN2A (10C) protein levels in caffeine-induced wakefulness mice. GluA1: glutamate AMPA type receptor 1, GluN1: glutamate NMDA type receptor 1, GluN2 A: glutamate NMDA type receptor 2 A. Data are expressed as percent of the control value. Blots were repeated at least 3 times. Western blot (10D) analysis was performed with actin included to ensure equal protein loading. Data are presented as a bar graph with means and standard deviations. a-e: Values within the bars with different subscripts are significantly different (ANOVA and Turkey's post-hoc test).
Figure 10B:
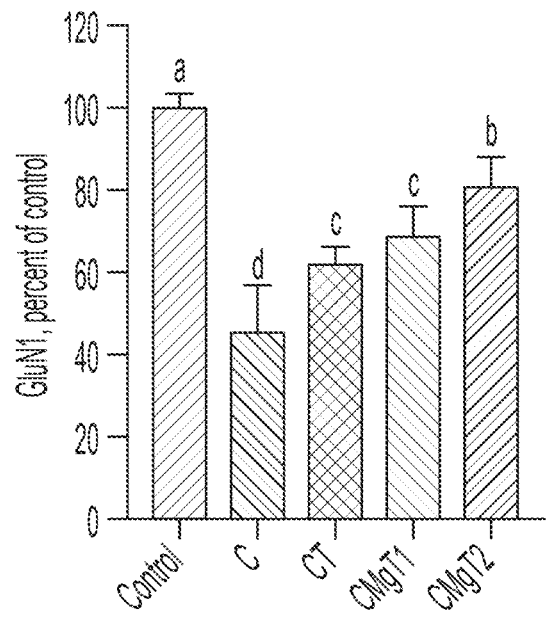
Figure 10C:
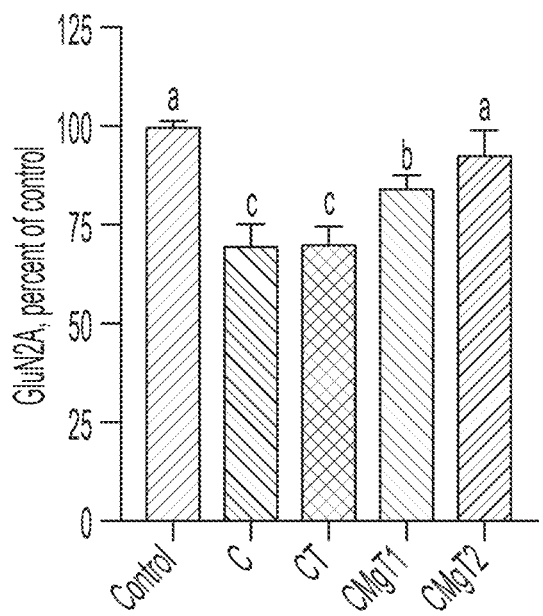
Figure 10D:
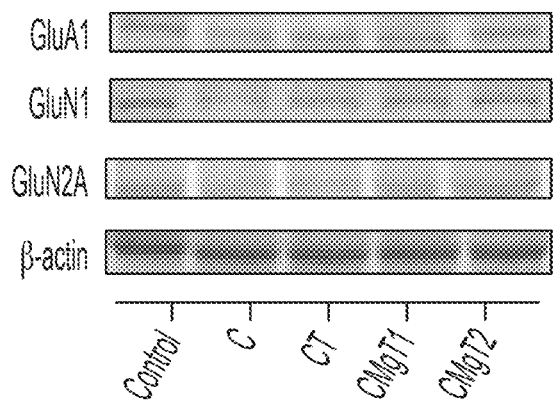

L-Theanine (50 g, 287 mmol) was slurried in 300 mL of methanol and one equivalent of 1 N NaOH solution was added dropwise until a clear solution was obtained. Then a solution of magnesium chloride hexahydrate (29 g, 144 mmol) in 145 mL of methanol was added. A clear solution resulted. Volatile solvents were removed by evaporation under vacuum. Acetonitrile was added, and the slurry was sonicated in an attempt to purify. After removal of the solvent under vacuum, the residual solid was dried under high vacuum. About 60 g of magnesium di-L-theanate (57% of theoretical) was thus obtained. The $^1$H-NMR spectrum of magnesium di-L-theanate (FIG. 6) confirms that the salt was successfully prepared. A sample was submitted for magnesium analysis. The result confirmed that 5.19% by weight magnesium was present vs. a theoretical value of 5.97% by weight, indicating a purity of 87%. Chloride analyses confirmed that NaCl was also present. No practical means for removing sodium chloride was identified. Thus, this composition comprises a magnesium di-L-theanate composition co-formulated with the excipient sodium chloride.

Example 5. Effects of Theanine and Compositions of the Invention on Sleep

Background and Objective: Caffeine, a well-known behavioral stimulant, is thought to exert its central nervous system effects primarily through adenosine receptor blockade. [4] Caffeine produces a variety of sleep disturbances, including reduction of total sleep time, prolonged latency of sleep onset, and increased wakefulness in humans and rats.[19, 21]L-theanine has various pharmacological actions such as promoting feelings of calmness, decreasing alertness, and anti-stress effects.[8, 15] Additionally, Kakuda et al. showed that by measuring electroencephalography (EEG) in rats, intravenous L-theanine at a dose higher than 0.78 mg/kg could inhibit the stimulatory action of caffeine. [13]

The present study was designed to investigate the effects of different forms of theanine, including L-theanine and Magnesium (Mg) Theanate, a novel form of theanine, on sleep and related behaviors in rodent models. For the analysis of sleep quality, the effect of different forms of theanine on brain waves was studied by electrocorticography (ECoG). In addition, neurotransmitter receptor binding activity of different forms of theanine and possible sleep-promoting substances was evaluated.

Material and Methods

Animals and Experimental design: Seven male BALB/c mice per treatment arm (age: 8 weeks, weight: 180±20 g) were housed in a controlled environment with a 12:12-h light-dark cycle at 22° C. and were provided with mice chow and water ad libitum. All experiments were conducted under the National Institutes of Health's Guidelines for the Care and Use of Laboratory Animals and approved by the Ethics Committee of the Medipol University.

Drugs and materials: Study product was provided by Nutrition21 LLC (Mg-Theanate #1=lot AA209-122-20, Mg-Theanate #2=lot BLS-DN 13). L-theanine and caffeine were dissolved in distilled water. The concentration of each drug solution was adjusted so that the volume injected was constant at 1.0 ml/kg BW. All drug solutions were prepared fresh daily, and were administered intraperitoneally (i.p.). Previous studies showed that caffeine-induced insomnia will be dose-dependent with 7.5 mg/kg i.p. caffeine maintaining wakefulness for at least 2 h (Kwon et al., 2006).

Experiment 1: Caffeine-Induced Wakefulness

Procedures—In order to monitor the effects of caffeine and different forms of theanine on brain activity, electrocorticography (ECoG) recording was performed. Animals were anesthetized with urethane (1.25 mg/kg, i.p., Sigma U2500). Body temperature was maintained between 36.5 and 37° C. with homeothermic blanket. Mice were stabilized under a stereotaxic frame (World Precision Instruments, Berlin; Germany) and an incision was made on the skin along the anterior/posterior line of the skull. The left cortex was removed gently with a dental drill (Marothon-3; Korea). Two Ag—AgCl sphere electrodes were placed over the left hemisphere with the reference electrode attached on the pinna. The mice received drug injections at 13:20 and 13:30 according to the predetermined treatment plan as follows:

1) Control: Saline followed by saline;
2) C (Positive Control): Caffeine followed by saline;
3) CT: Caffeine followed by theanine (20 mg theanine/kg);
4) CMgT1: Caffeine followed by Mg theanate #1 (20 mg theanine/kg);
5) CMgT2: Caffeine followed by Mg theanate #2 (20 mg theanine/kg).

Electrical activity of the brain was monitored for 90 minutes following the caffeine injection and spike frequency/spike amplitude analysis was performed using the Labchart 7.3.3 program. Ninety minutes after the caffeine injection, animals were deeply anesthetized with 4% isofluorane (30% O2, remainder N20). Brains were rapidly removed, frozen on dry ice and stored at −80° C. until analyses could be performed.

Biochemical and Oxidative Stress Markers—Serum melatonin, serotonin, and dopamine were measured using ELISA kits. Brain levels of malondialdehyde (MDA) were measured by HPLC. Brain activities of superoxide dismutase (SOD), catalase (CAT) and glutathione peroxidase (GSHPx) were measured using ELISA kits for each analyte.

Protein analyses—Protein concentrations were determined using Western blot analysis. Fifty μg of protein was electrophoresed on 4-15% Tris-Glycine polyacrylamide gels and then was transferred to Immobilon-P PVDF membranes, blocked for 1 h in 5% skim milk and incubated overnight at 4° C. with either GABAA R2, $GABA_B$ R1, GABAA-R2, 5HT1A, GluA1, GluN1, GluN2 A, iNOS, e-NOS, Bcl-2, Bax, Caspase-3, and Caspase-9. Membranes were then incubated with horseradish peroxidase (HRP) conjugated IgG secondary antibody. Bands were quantified using Image software and normalized to actin as a loading control. Serum biochemical parameters were determined using a biochemical analyzer.

Results

TABLE 3

Summary of Group Differences in Brain Responses in the Caffeine-induced Wake Mouse

Sleep latency

Caffeine: The sleep latency period doubled to about 2 minutes in caffeine-treated animals.
+ Theanine: The sleep latency period increased from about 1 to about 1.5 minute, a significantly shorter period than found in caffeine-treated animals.
+ Mg Theanate Composition: The sleep latency period increased from slightly less than 1 to slightly more than 1 minute, a significantly shorter period than found in caffeine-treated animals and different from theanine-treated animals.

Sleep duration

Caffeine: The sleep duration period decreased from over 60 minutes to about 30 minutes in caffeine-treated animals.
+ Theanine: The sleep duration period was about 40 minutes, significantly different from caffeine-treated animals.
+ Mg Theanate Composition: The sleep duration period of about 50 minutes was greatly normalized, as compared to either caffeine- or theanine-treated animals.

Number of animals falling asleep

Caffeine: only 50% of the group fell asleep
+ Theanine: 62.5% of the group fell asleep
+ Mg Theanate Composition: 70% of the group fell asleep

Electrical activity over 120 minutes

Caffeine: The amplitude of brain waves was comparable to that of awake animals in the control group. The spike frequency increased significantly within 30 minutes and was maintained for the 120 minute study period, reflecting the metabolic disruption in the brain caused by caffeine.

TABLE 3-continued

Summary of Group Differences in Brain Responses in the Caffeine-induced Wake Mouse + Theanine: Within about 30 minutes, the amplitude of brain waves increased significantly and was maintained throughout the 120 minute study period. Spike frequency was significantly reduced, as compared to caffeine-treated animals.
+ Mg Theanate Composition: Within about 30 minutes, the amplitude of brain waves increased significantly and was maintained throughout the 120 minute study period. Spike frequency was significantly reduced and comparable to caffeine/theanine-treated animals.
Neurotransmitter levels (brain serotonin, dopamine, and melatonin)

Caffeine: Levels of all three neurotransmitters were significantly reduced, reflecting the metabolic disruption in the brain caused by caffeine.
+ Theanine: As compared to caffeine-treated animals, levels of all three neurotransmitters were partially restored to control levels.
+ Mg Theanate Composition: As compared to caffeine- and caffeine/theanine-treated animals, levels of all three neurotransmitters were more significantly restored to control levels.
Brain antioxidant status (MDA, SOD, CAT, GSHPx)

Caffeine: The level of MDA (an indicator of oxidative stress) was significantly increased, and the levels of protective enzymes (SOD, CAT, GSHPx) were significantly reduced, reflecting the metabolic disruption in the brain caused by caffeine.
+ Theanine: The level of MDA was increased and the levels of protective enzymes were decreased, but the changes were not as great as those shown by caffeine treatment.
+ Mg Theanate Composition: Although the level of MDA was increased and the levels of protective enzymes were decreased, the adverse changes were not as great as those shown by caffeine/theanine treatment.
Brain cell survival (Bax, Bcl-2, Caspase-3, eNOS, and iNOS-indicators of cell damage that may lead to apoptosis)

Caffeine: Decreases in the cytosolic levels of Bax, Bcl-2, and Caspase-3, as well as the increases in eNOS and iNOS reflect the metabolic disruption and cellular damage induced by caffeine.
+ Theanine: Administration of theanine caused trends toward normalization of these indicators of cell damage.
+ Mg Theanate Composition: Administration of Mg Theanate Composition caused significant normalization of all of these indicators of cell damage, improvements that exceeded those of theanine alone.
GABA and other neurotransmitter receptors Caffeine: Administration of caffeine significantly reduced the transcript levels of neurotransmitter receptors of all types, including glutamate-AMDA and glutamate-NMDA receptor subunits, as compared to control.
+ Theanine: Administration of theanine partially diminished the severe reductions in receptor transcript levels.
+ Mg Theanate Composition: Administration of Mg Theanate Compositions significantly diminished the reductions in receptor transcript levels, as compared to both caffeine- and caffeine/theanine-treated animals.

Experiment II—Pentobarbital-Induced Sleep

Pentobarbital-induced sleep was performed according to published methods with slight modifications. Mice were fasted for 24 h prior to the experiment. Each test article was dissolved or suspended in physiological saline and then was administered per os. The groups were administered doses of 20 mg/kg theanine, Mg-theanate #1 (20 mg theanine/kg), and Mg-theanate #2 (20 mg theanine/kg), respectively. Forty-five minutes later, a hypnotic dose of pentobarbital (42 mg/kg) was injected into the left side of the abdomen. After injection, the mice were placed in individual cages and subjected to measurements of sleep latency and duration. Sleep latency was defined as the period between pentobarbital injection and the loss of righting reflex (sleep onset), and sleep duration denoted the time elapsed between loss of the righting reflex and recovery. Mice that failed to fall asleep within 10 min after pentobarbital injection were excluded from the experiments.

Statistical Analyses—Data are shown as mean±SEM. Sample size was calculated based on a power of 85% and a p-value of 0.05. Given that assumption, a sample size of seven per treatment was calculated. The data were analyzed using the GLM procedure of SAS (SAS Institute: SAS User's Guide: Statistics). The treatments were compared using ANOVA and Student's unpaired t-test; $P<0.05$ was considered statistically significant.

Results—As expected, administration of L-theanine prior to pentobarbital injection significantly decreased the sleep latency period and significantly increased the duration of sleep. Unexpectedly, administration of equivalent doses of theanine as magnesium di-L-theanate compositions significantly and more effectively decreased the sleep latency period and significantly and more effectively increased the sleep duration period as compared to the effects of theanine. Surprisingly, animals receiving magnesium di-L-theanate compositions were significantly more likely to fall asleep within the 10 minute limit as compared to animals receiving theanine itself.

Additional features, advantages, and embodiments of the invention may be set forth or apparent from consideration of the following detailed description, drawings, and claims.

Moreover, it is to be understood that both the foregoing summary of the invention and the following detailed description are exemplary and intended to provide further explanation without limiting the scope of the invention as claimed.

What is claimed is:

1. A composition comprising magnesium di-L-theanate:

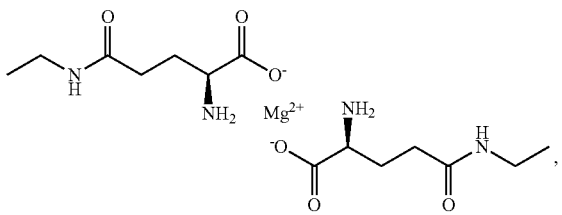

wherein the magnesium di-L-theanate exhibits an optical rotation of 3-4°.

2. A method of improving sleep in a subject in need thereof, the method comprising the step of administering an effective amount of magnesium di-L-theanate, wherein the effective amount is about 20 mg/kg body weight, wherein the effective amount is sufficient to decrease sleep latency and/or increase length of sleep, wherein said magnesium di-L-theanate is a solid having a molecular structure of

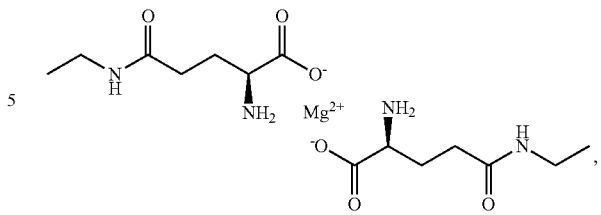

an optical rotation of 3-4°, and contains 5.5-6.0% by weight magnesium and 94.0-94.5% by weight L-theanate.

3. The method of claim 2, wherein the magnesium di-L-theanate is formulated for administration to a mammal.

4. The method of claim 3, wherein the step for administration is administration by mouth.

5. A method of preparation for a magnesium di-L-theanate compound, comprising the steps of:
   (a) Dissolving 2 mole equivalents of L-theanine and 1 mole equivalent of magnesium ethoxide in an aqueous alcohol solution, wherein the alcohol in said aqueous alcohol solution is ethanol or methanol;
   (b) Allowing said solution to stir at ambient or elevated temperature until a clear solution is obtained;
   (c) Removing volatile solvents from said clear solution by evaporation to provide a solid;
   (d) Dispersing the solid in an immiscible solvent and removing said solvent by filtration to provide a solid filtrand of purified magnesium di-L-theanate;
   (e) Drying said solid filtrand to remove residual solvents and provide purified magnesium di-L-theanate.

* * * * *